(12) United States Patent
Nihalani

(10) Patent No.: US 8,491,641 B2
(45) Date of Patent: Jul. 23, 2013

(54) PEDICLE SCREWS AND DYNAMIC ADAPTORS

(75) Inventor: Raj Nihalani, Irvine, CA (US)

(73) Assignee: Spinofix, Inc., Irvine, CA (US)

( * ) Notice: Subject to any disclaimer, the term of this patent is extended or adjusted under 35 U.S.C. 154(b) by 233 days.

(21) Appl. No.: 12/892,826

(22) Filed: Sep. 28, 2010

(65) Prior Publication Data

US 2012/0078307 A1 Mar. 29, 2012

(51) Int. Cl.
*A61B 17/70* (2006.01)

(52) U.S. Cl.
USPC ............ 606/269; 606/267; 606/266; 606/270

(58) Field of Classification Search
USPC .................................................. 606/250–278
See application file for complete search history.

(56) References Cited

U.S. PATENT DOCUMENTS

| | | | |
|---|---|---|---|
| 5,207,678 A | 5/1993 | Harms et al. | |
| 5,360,431 A | 11/1994 | Puno et al. | |
| 5,466,237 A | 11/1995 | Byrd, III et al. | |
| 5,474,555 A | 12/1995 | Puno et al. | |
| 5,782,833 A * | 7/1998 | Haider | 606/266 |
| 6,355,040 B1 * | 3/2002 | Richelsoph et al. | 606/272 |
| 6,626,909 B2 | 9/2003 | Chin | |
| 7,250,060 B2 | 7/2007 | Trieu | |
| 7,393,361 B2 | 7/2008 | Zubok et al. | |
| 7,621,953 B2 | 11/2009 | Braddock | |
| 7,794,478 B2 | 9/2010 | Nilsson | |
| 7,837,714 B2 | 11/2010 | Drewry et al. | |
| 8,361,123 B2 * | 1/2013 | Fanger et al. | 606/270 |
| 2001/0023350 A1 * | 9/2001 | Choi | 606/61 |
| 2004/0049274 A1 | 3/2004 | Reiley | |
| 2005/0113927 A1 | 5/2005 | Malek | |
| 2005/0228376 A1 | 10/2005 | Boomer et al. | |
| 2006/0079899 A1 | 4/2006 | Ritland | |
| 2006/0084991 A1 | 4/2006 | Borgstrom et al. | |
| 2006/0200130 A1 | 9/2006 | Hawkins et al. | |
| 2006/0229615 A1 | 10/2006 | Abdou | |
| 2006/0282078 A1 | 12/2006 | Labrom et al. | |
| 2007/0055242 A1 | 3/2007 | Bailly | |
| 2007/0135919 A1 | 6/2007 | Aebi et al. | |
| 2008/0033433 A1 | 2/2008 | Implicito | |
| 2008/0039844 A1 * | 2/2008 | Jackson | 606/61 |
| 2008/0172092 A1 | 7/2008 | Kraemer | |
| 2009/0076552 A1 * | 3/2009 | Tornier | 606/264 |
| 2009/0131984 A1 | 5/2009 | Linares | |

(Continued)

OTHER PUBLICATIONS

Phygen Laguna Pedicle Screw System Surgical Technique Guide, 24 pages, 2009.

(Continued)

*Primary Examiner* — Jan Christopher Merene
(74) *Attorney, Agent, or Firm* — Snell & Wilmer LLP

(57) ABSTRACT

The present invention may include a pedicle screw with a multifunctional adaptor, a strain reliever, and a dual-surface cap. The multifunctional adaptor may include a convex pivot ring for improving multi-axial movement and locking stability, an integrated locking mechanism for improving maneuverability, and an integrated compression member for improving the assembly process. The strain reliever may be formed along a neck of the pedicle screw for relieving mechanical stress asserted thereto, and thereby preventing a breakage thereof. The dual-surface cap may provide a slightly sloped surface for reducing the tension of the stabilizing rod. The present invention may also provide for a dynamic adaptor for flexibly connecting two stabilizing rods, which may be versatilely adapted to various pedicle screw configurations.

7 Claims, 24 Drawing Sheets

U.S. PATENT DOCUMENTS

| | | |
|---|---|---|
| 2009/0132052 A1 | 5/2009 | Baccelli et al. |
| 2009/0264926 A1 | 10/2009 | Taylor et al. |
| 2009/0265007 A1 | 10/2009 | Colleran |
| 2009/0318968 A1 | 12/2009 | Duggal et al. |
| 2009/0326580 A1 | 12/2009 | Anderson et al. |
| 2010/0087862 A1 | 4/2010 | Biedermann et al. |
| 2010/0234891 A1* | 9/2010 | Freeman et al. ............ 606/266 |
| 2010/0298891 A1* | 11/2010 | Jackson ............ 606/308 |

OTHER PUBLICATIONS

Biomet Spine Polaris 5.5 Surgical Technique, 28 pages, 2008.
Aesculap S4 Spinal System Posterior Thoracolumbar Stabilization System, 16 pages, 2008.

* cited by examiner

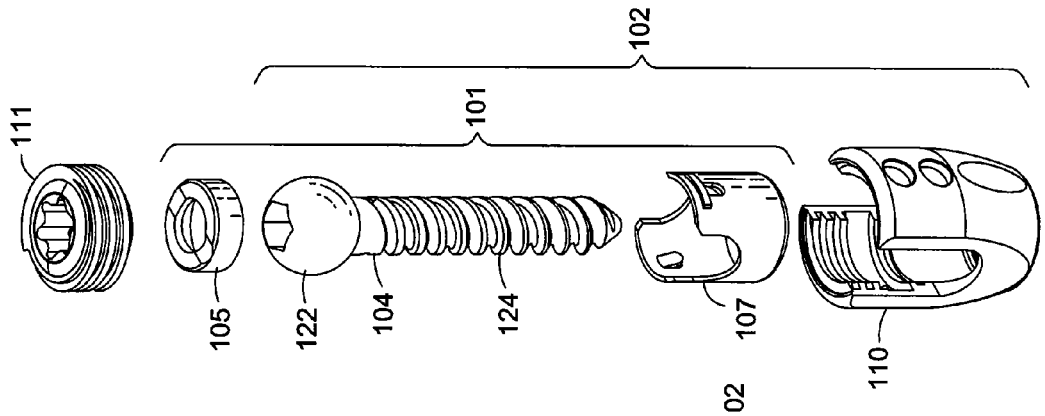
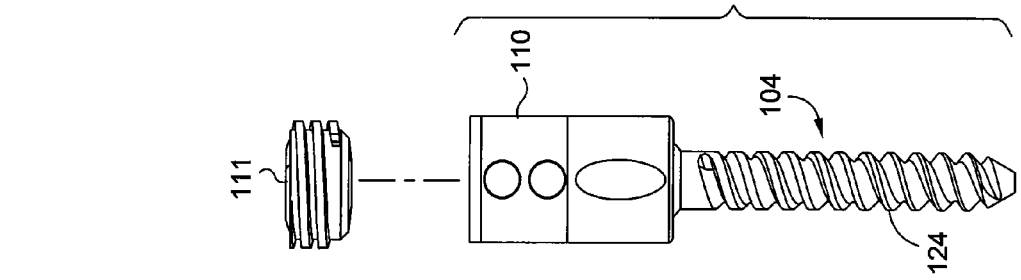
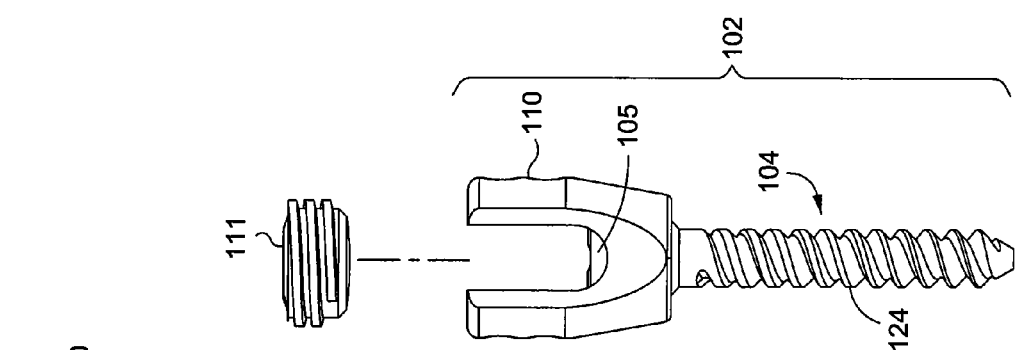
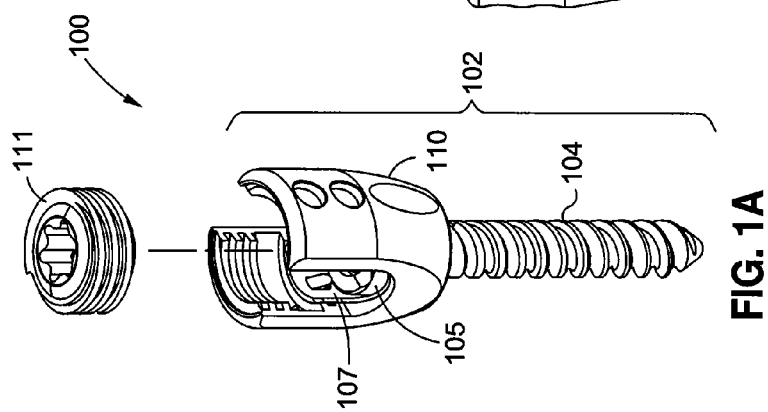

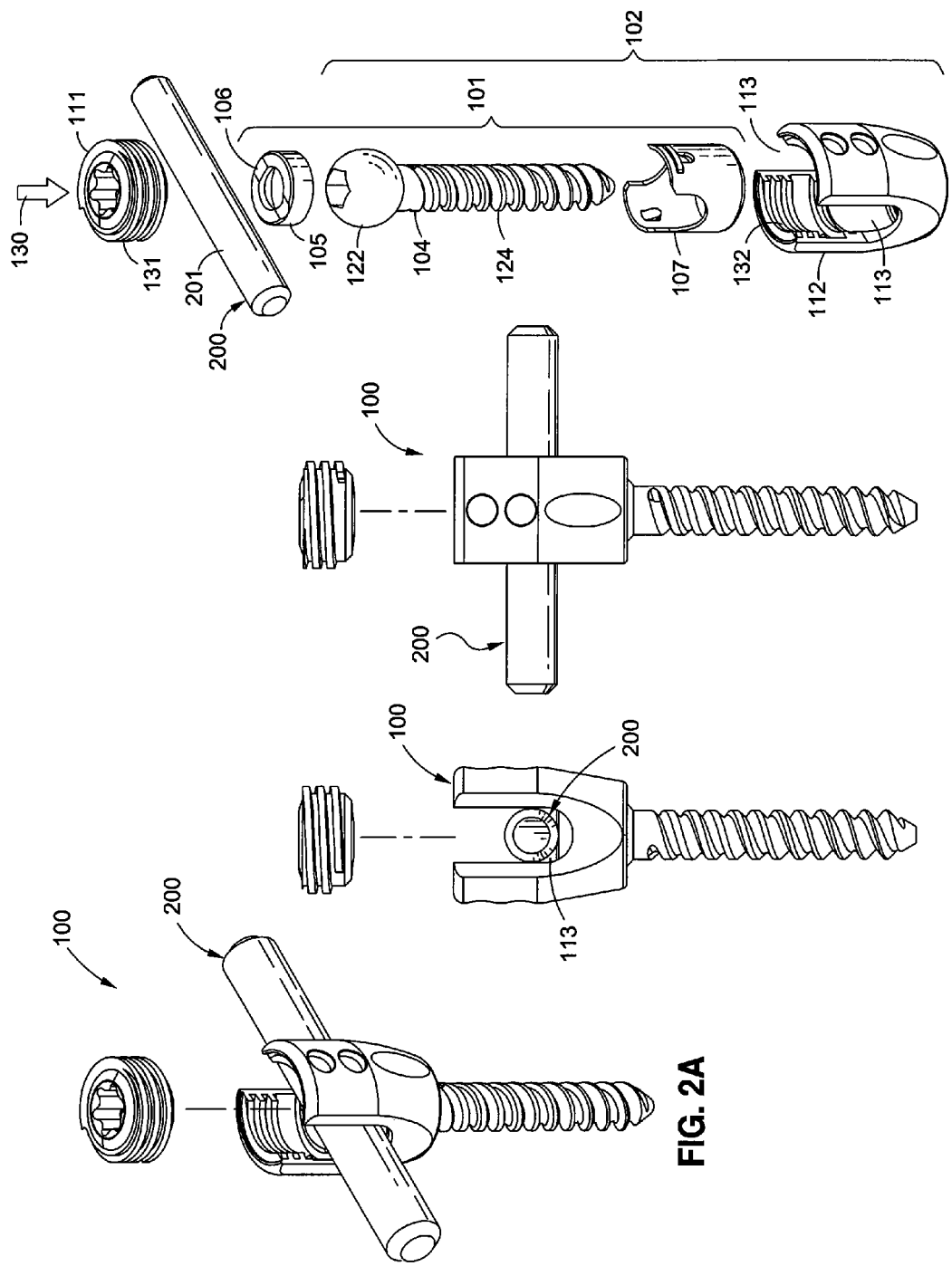

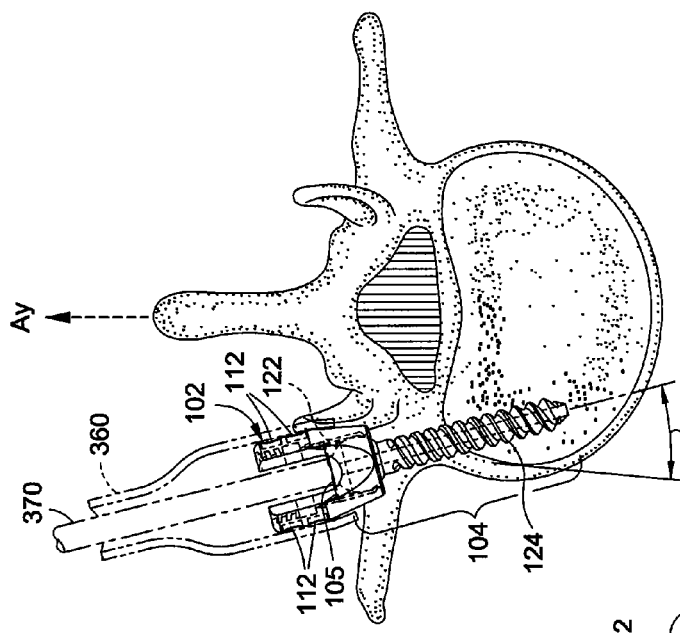
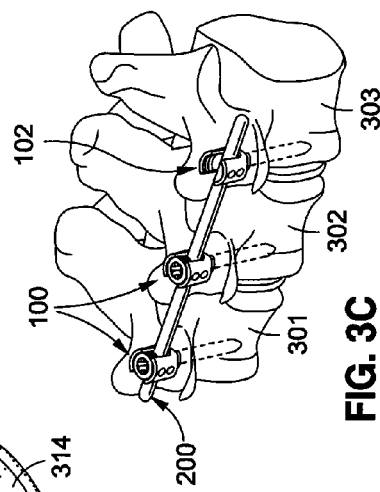
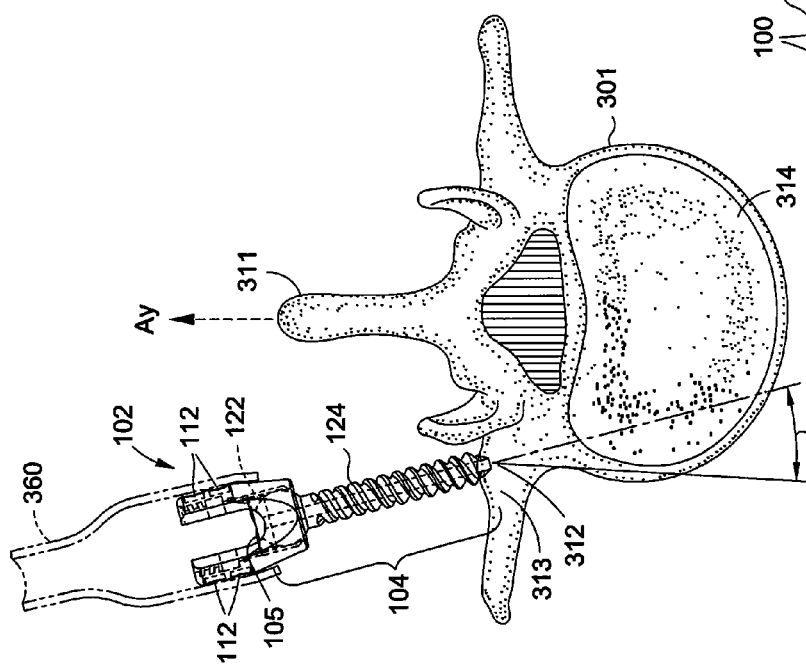
FIG. 3A
FIG. 3B
FIG. 3C

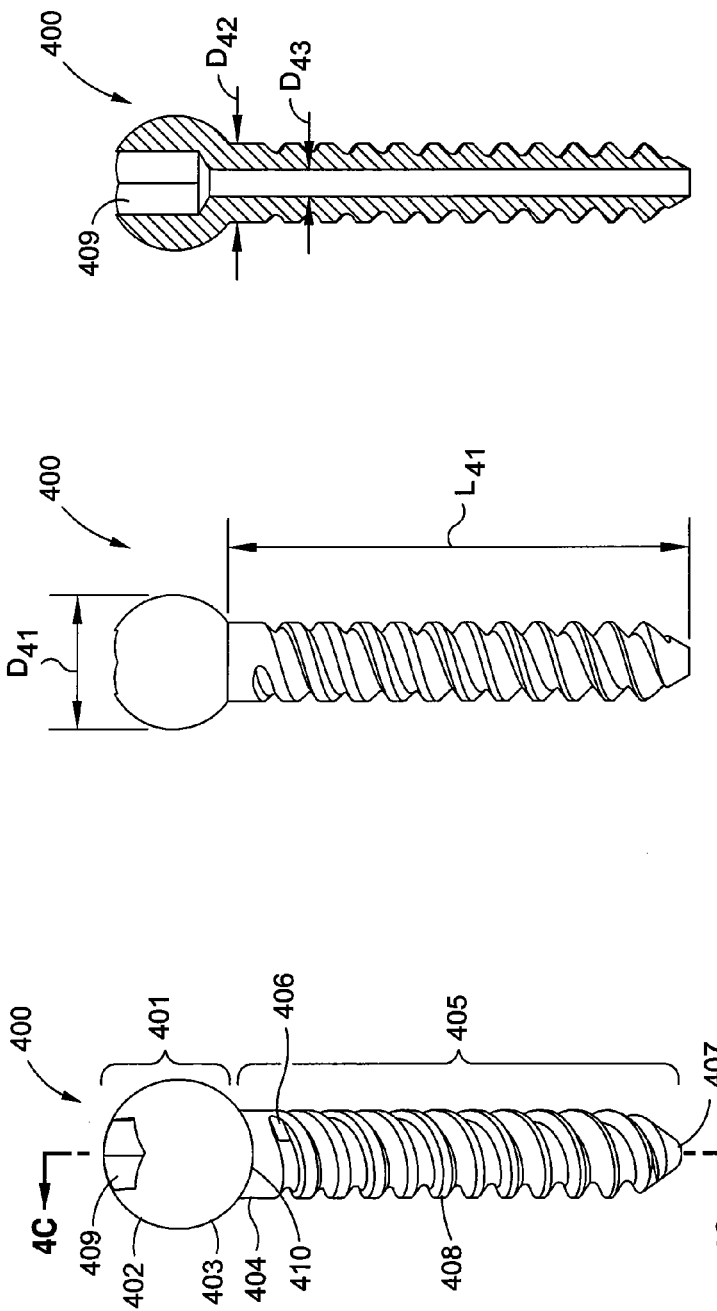

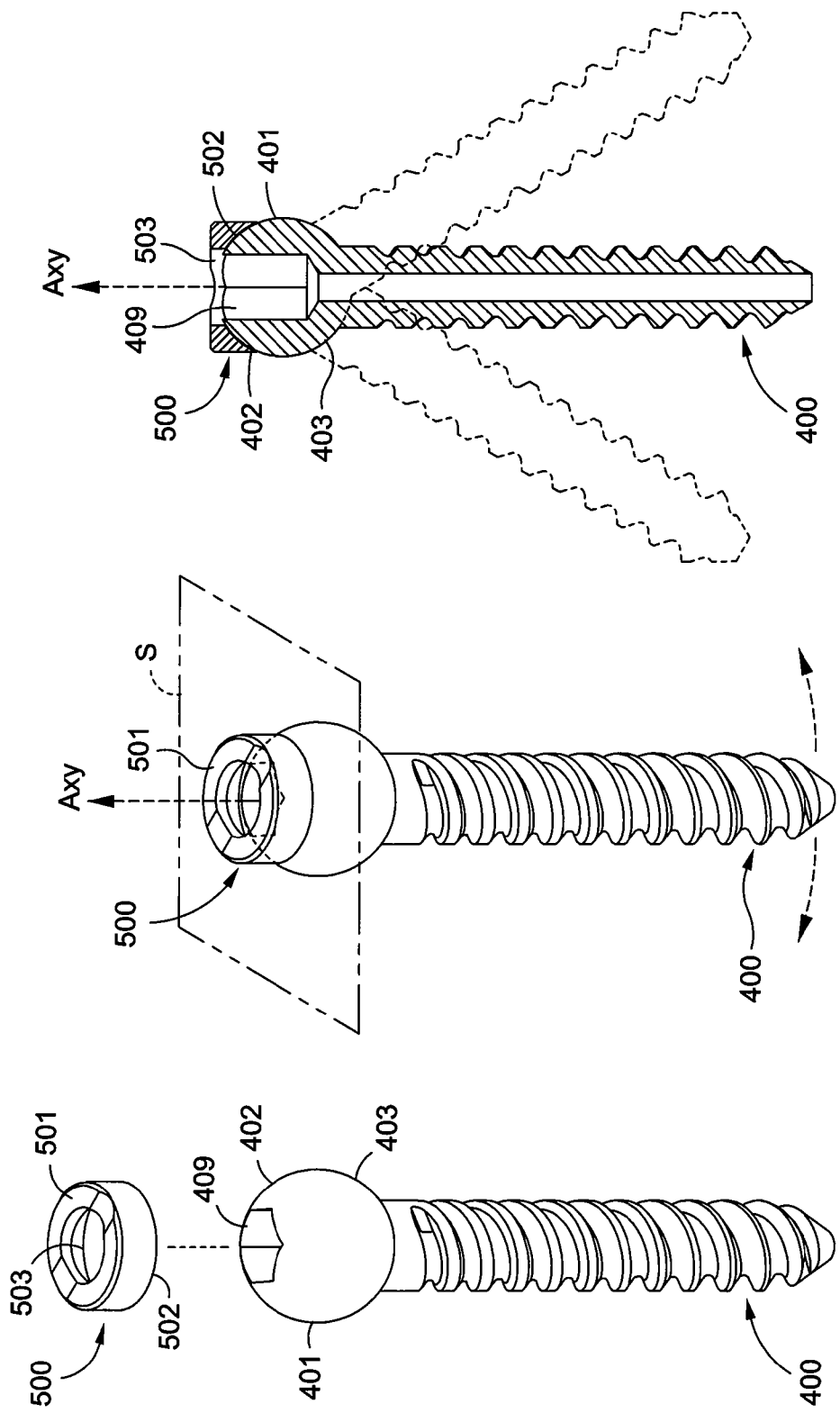

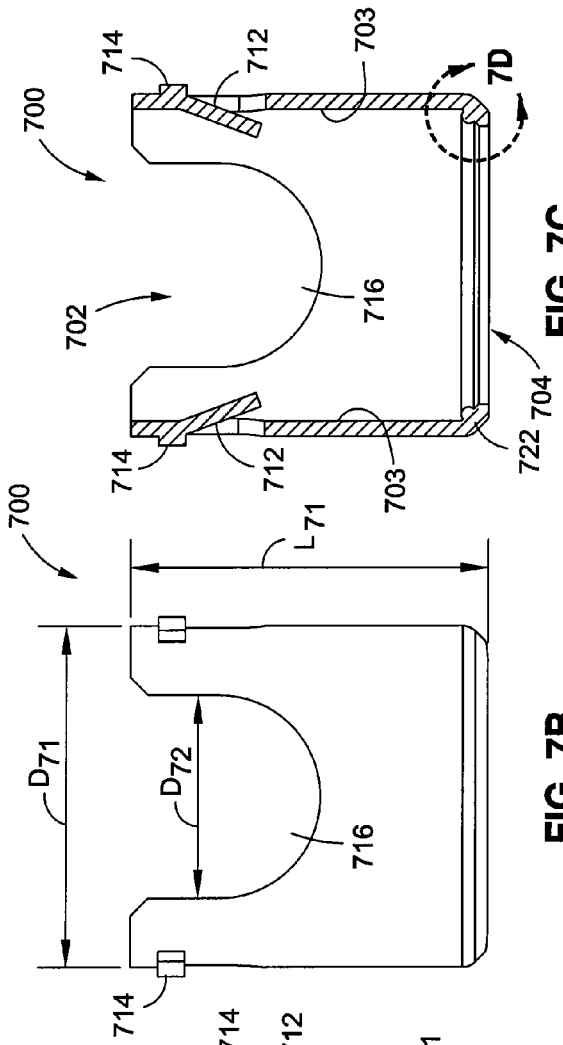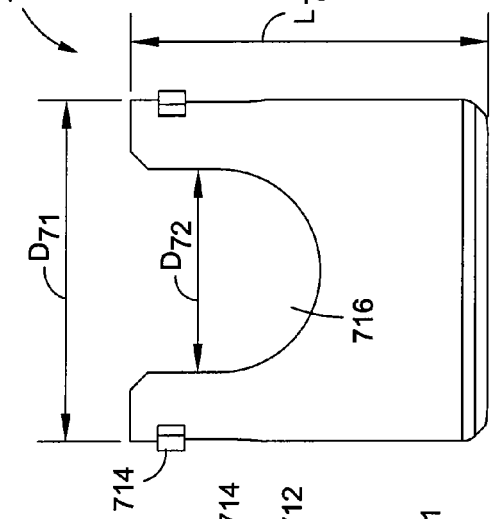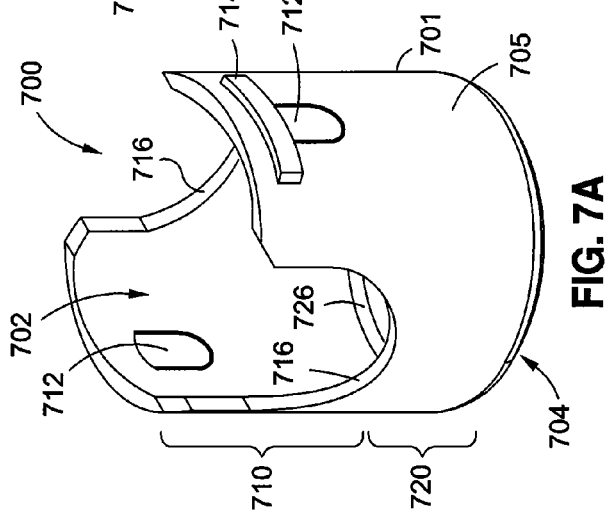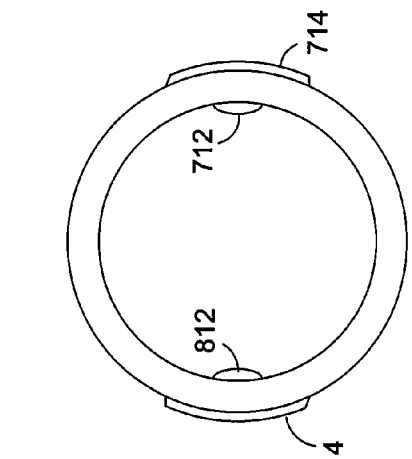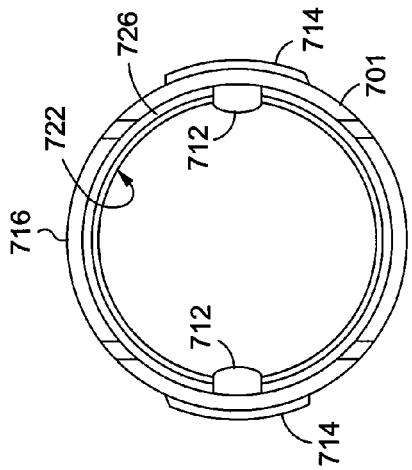
FIG. 7A
FIG. 7B
FIG. 7C
FIG. 7D
FIG. 7E
FIG. 7F

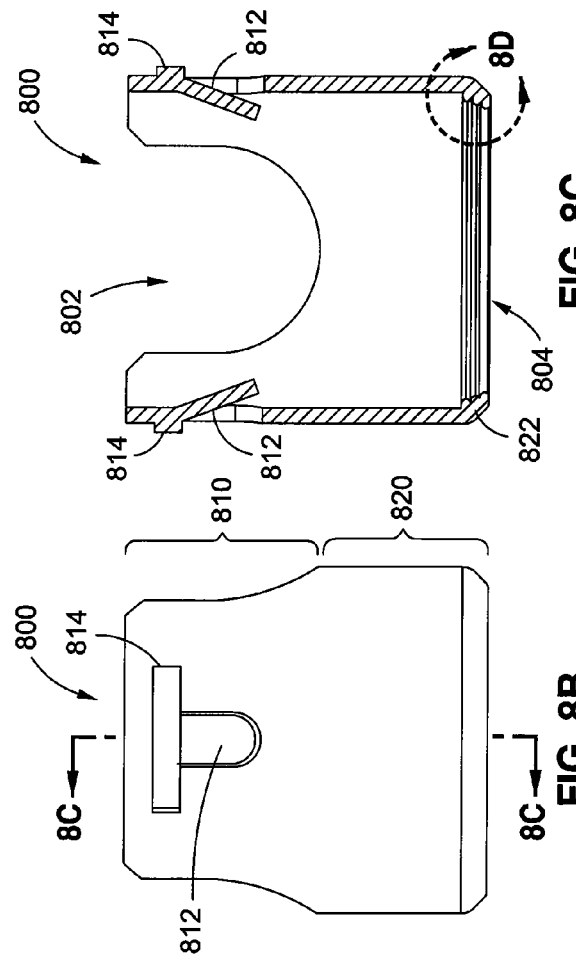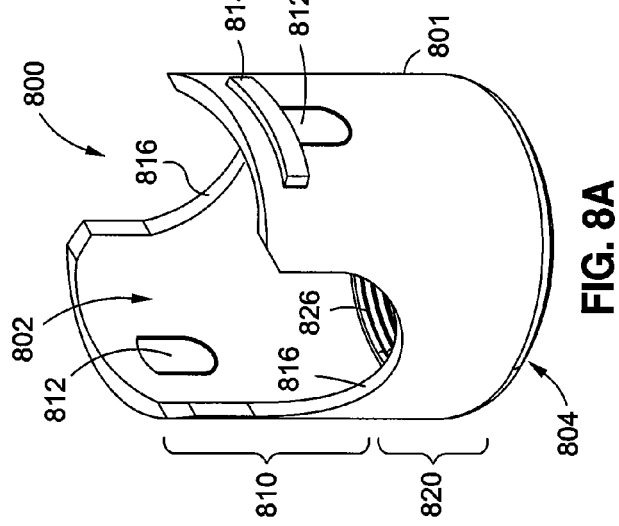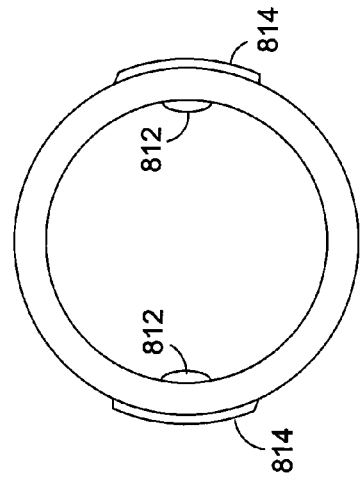

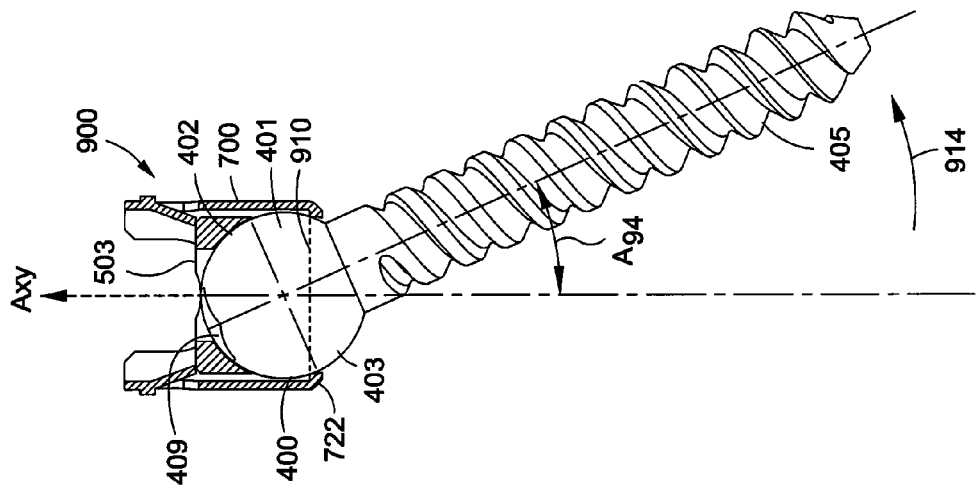
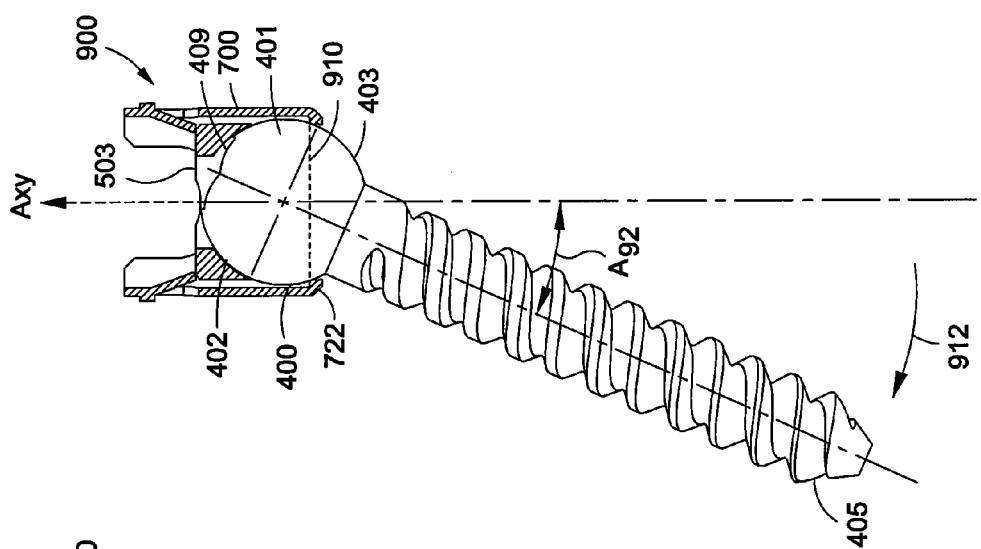
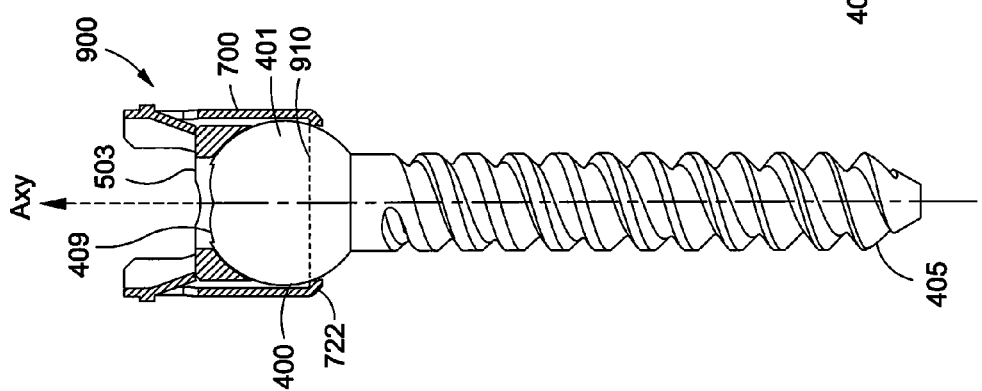

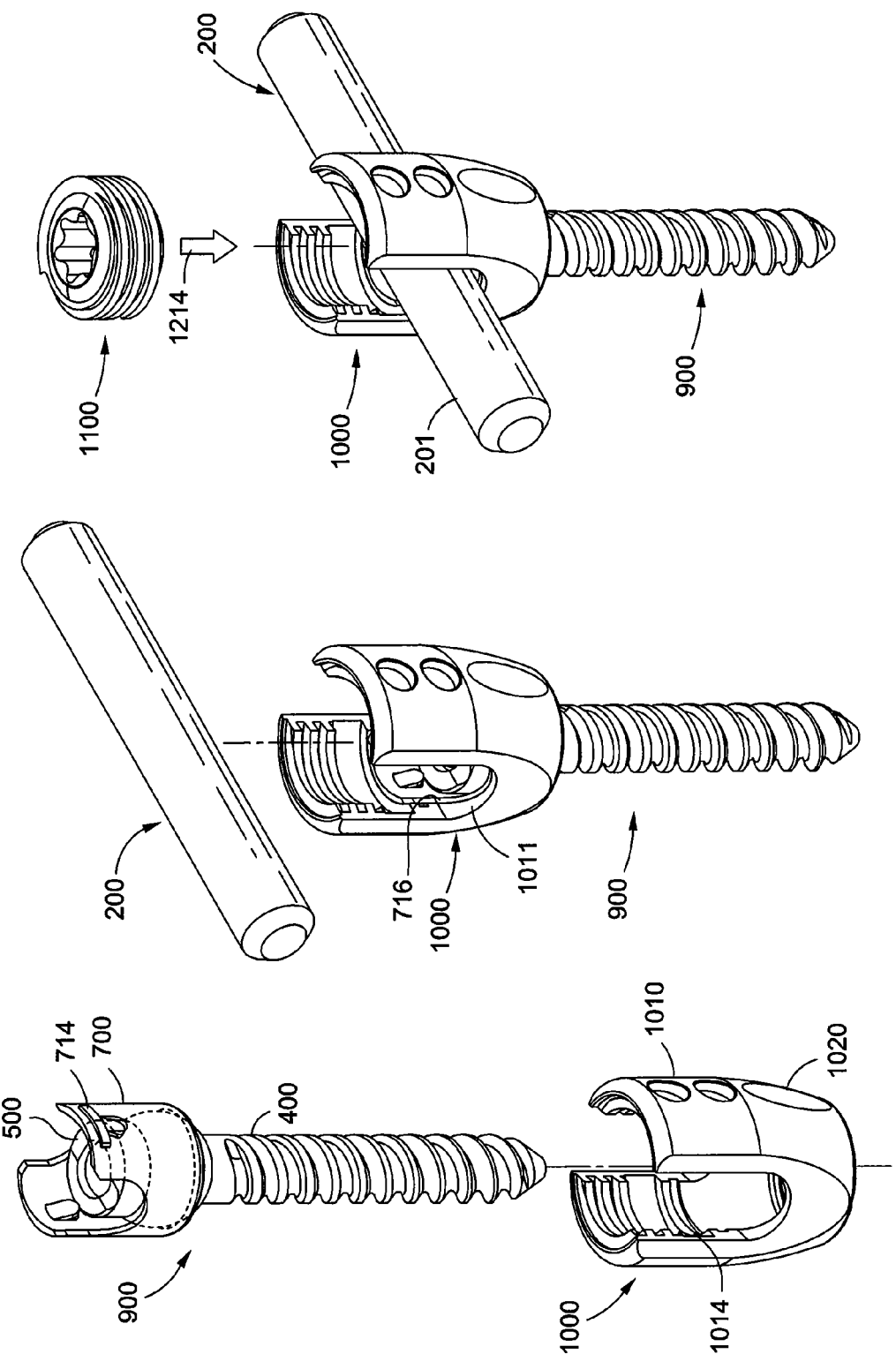

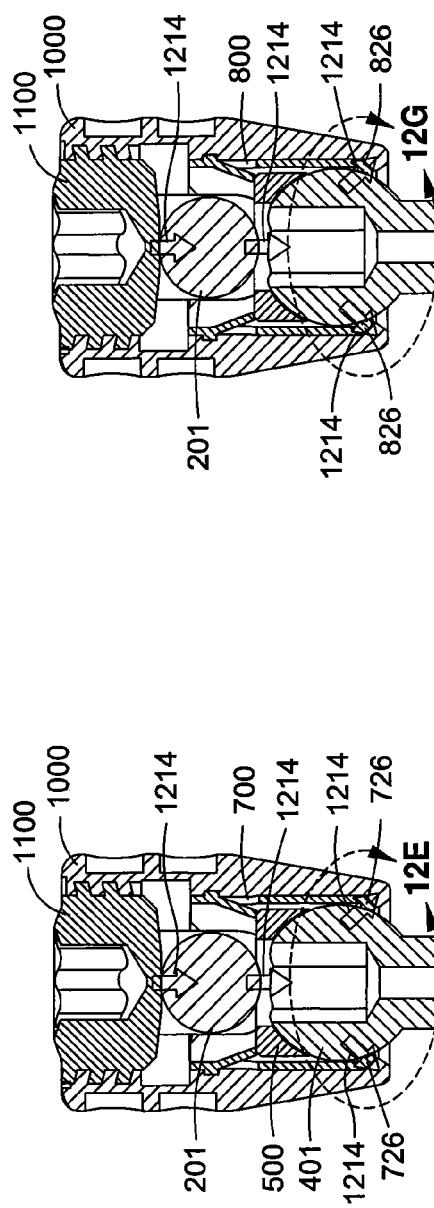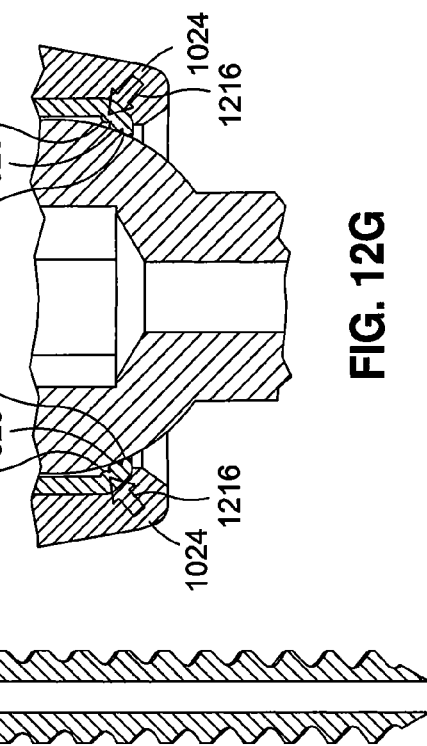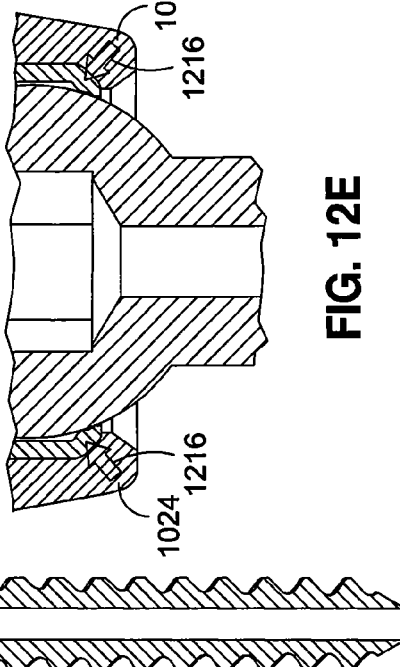
FIG. 12D
FIG. 12E
FIG. 12F
FIG. 12G

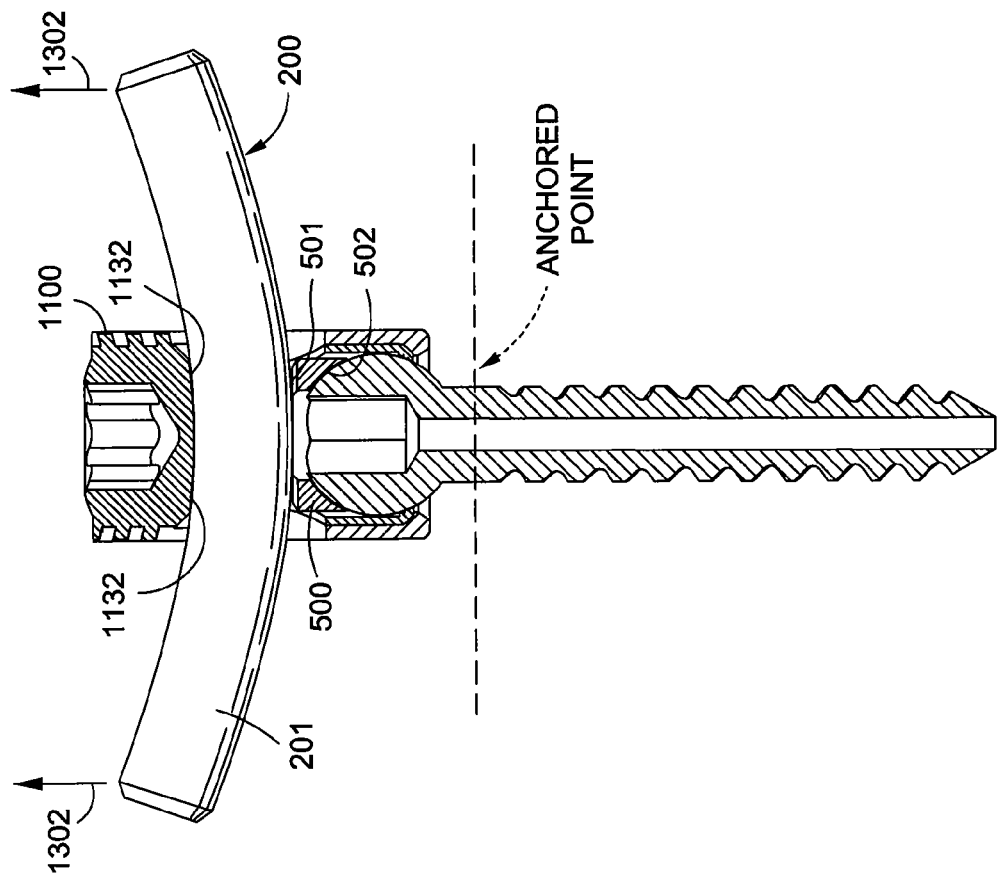
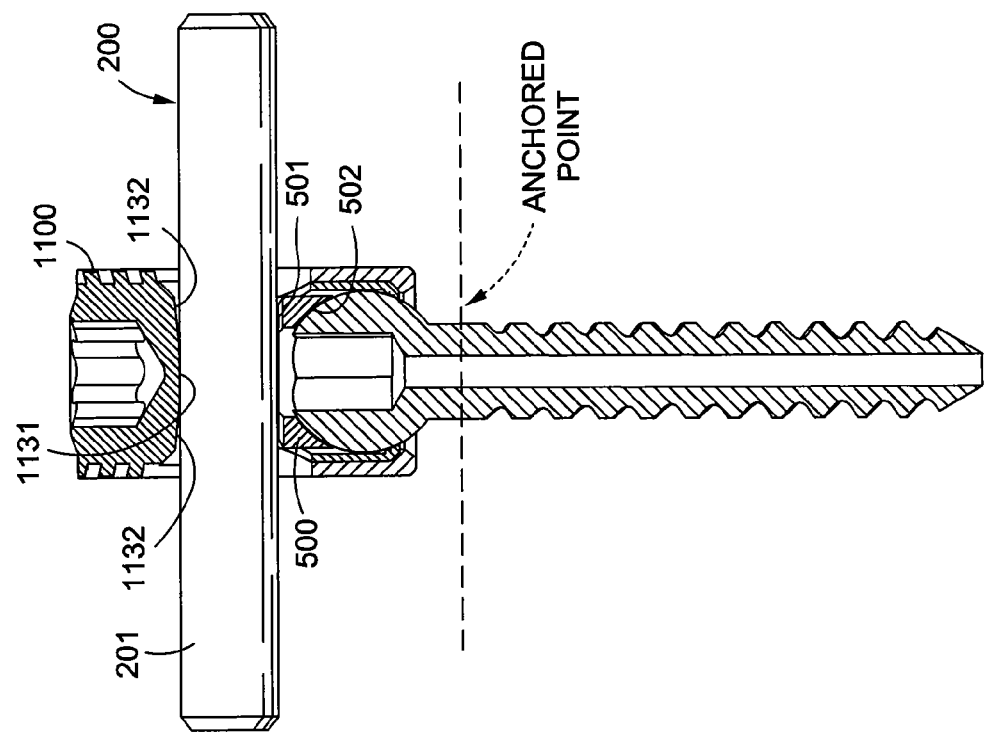

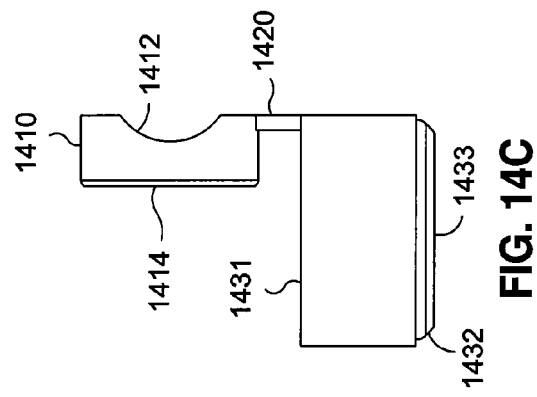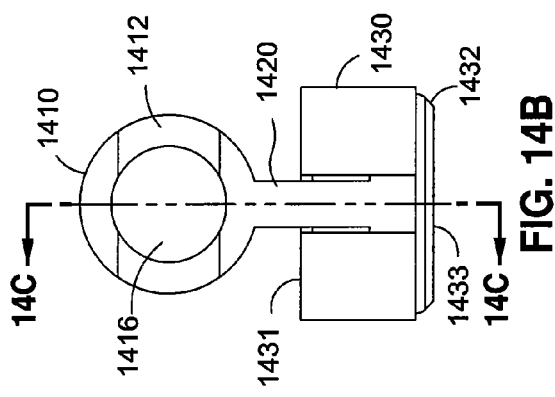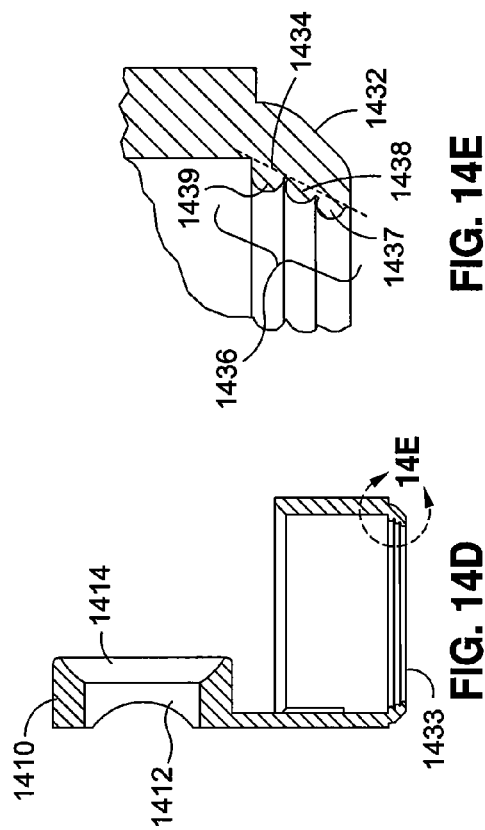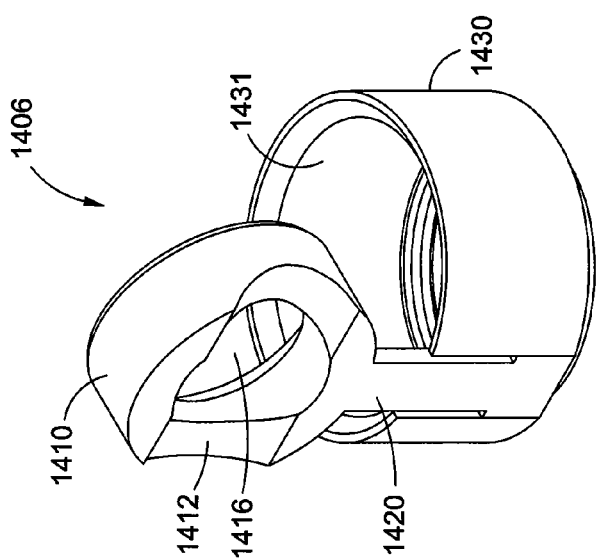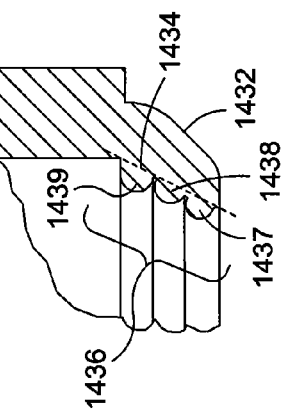

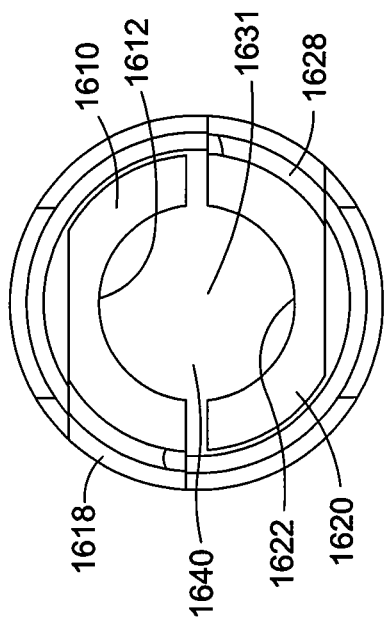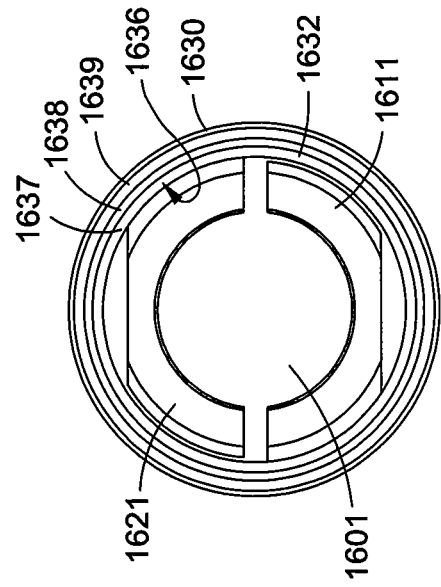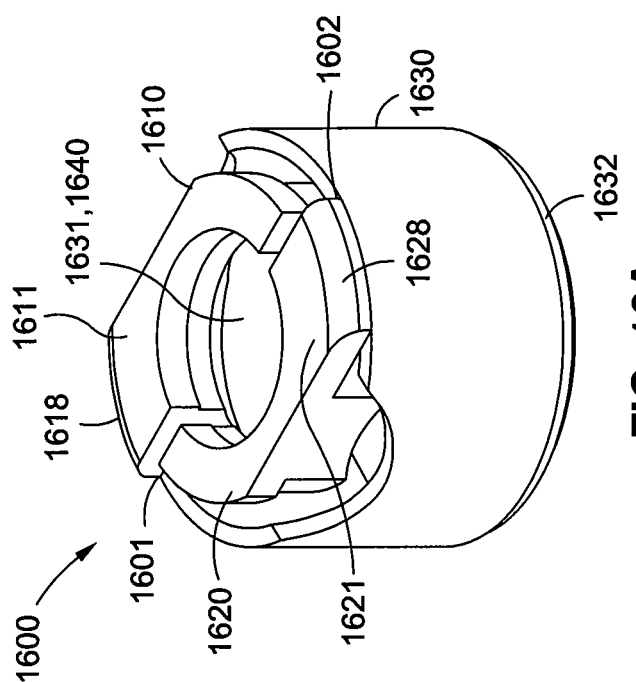

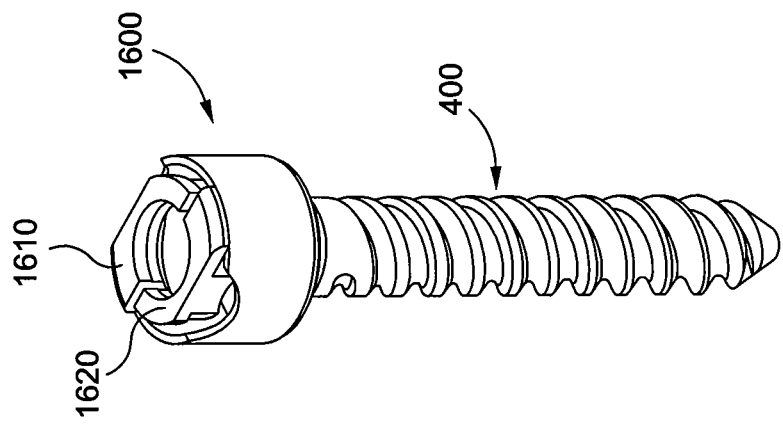
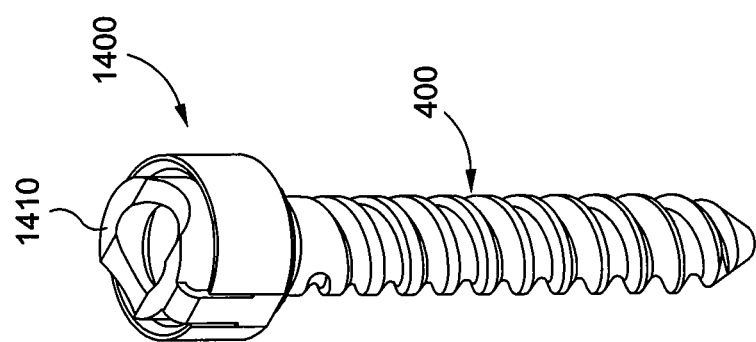
FIG. 17A
FIG. 17B

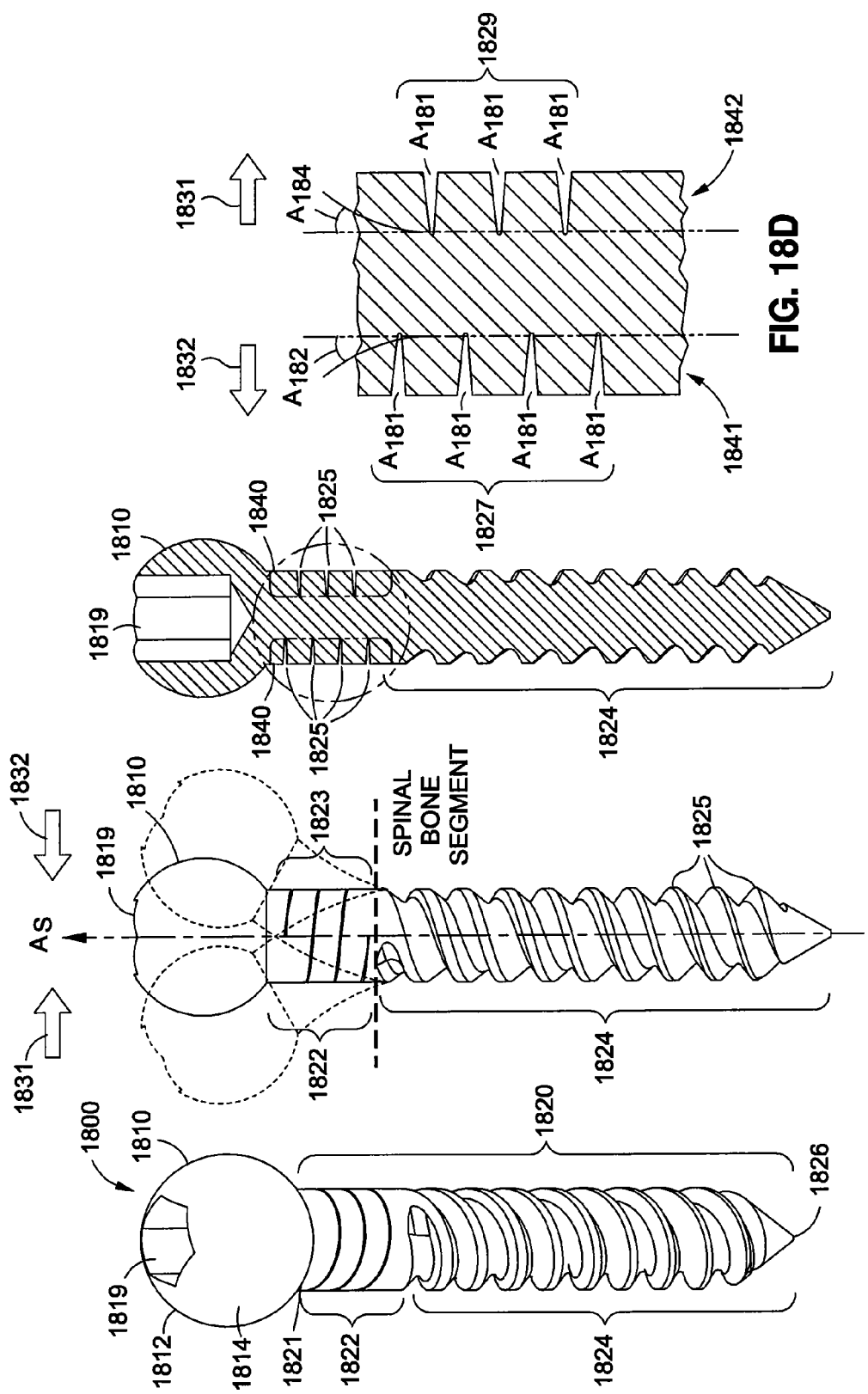

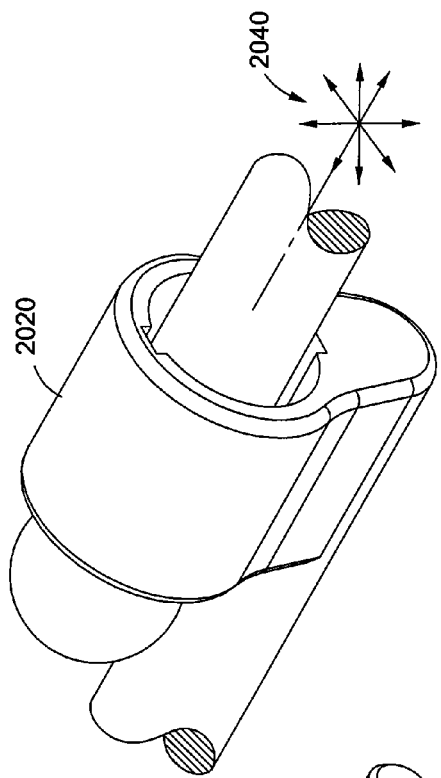
FIG. 20A
FIG. 20B
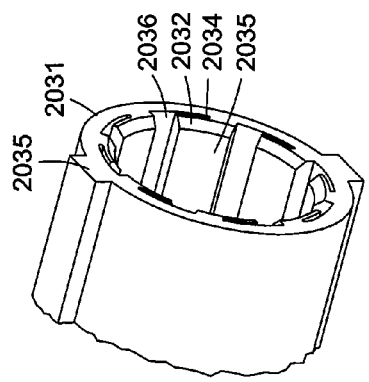
FIG. 20D
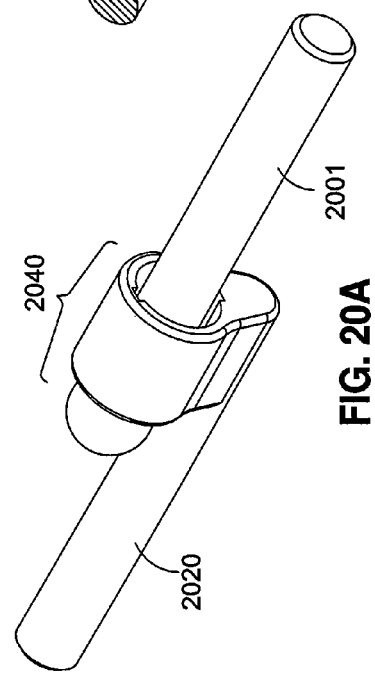
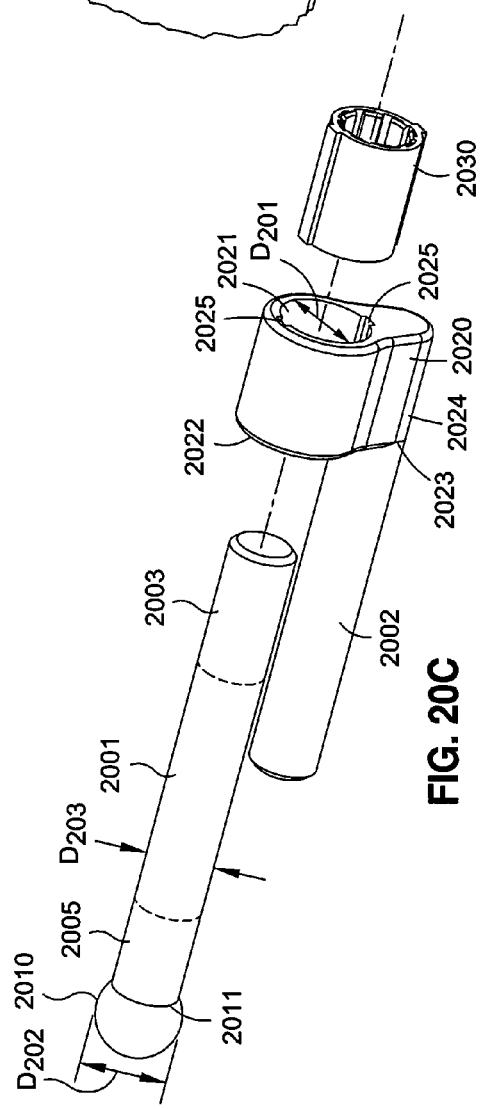
FIG. 20C

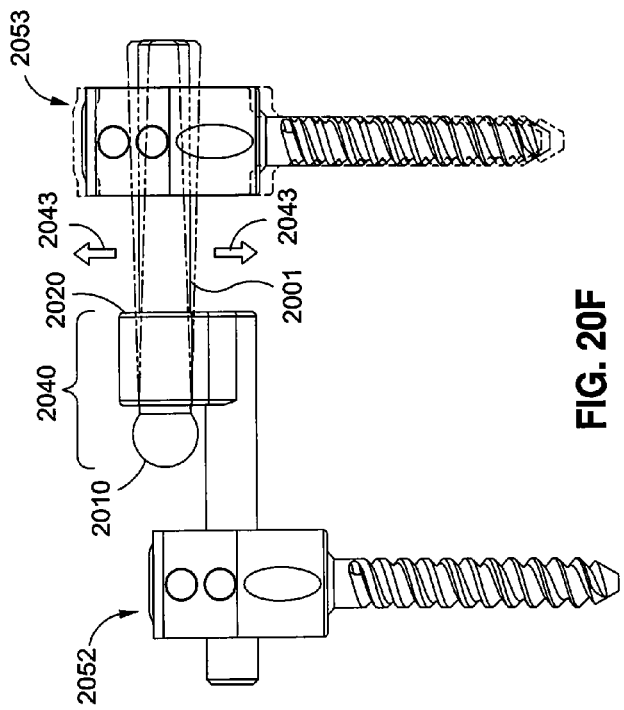
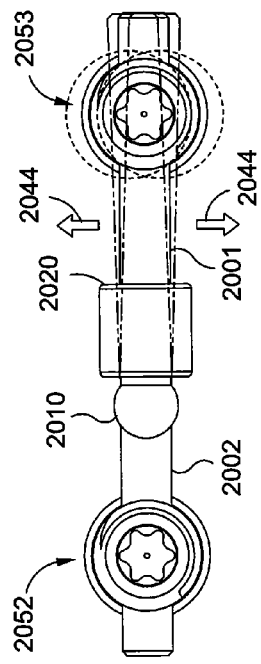
FIG. 20F
FIG. 20G
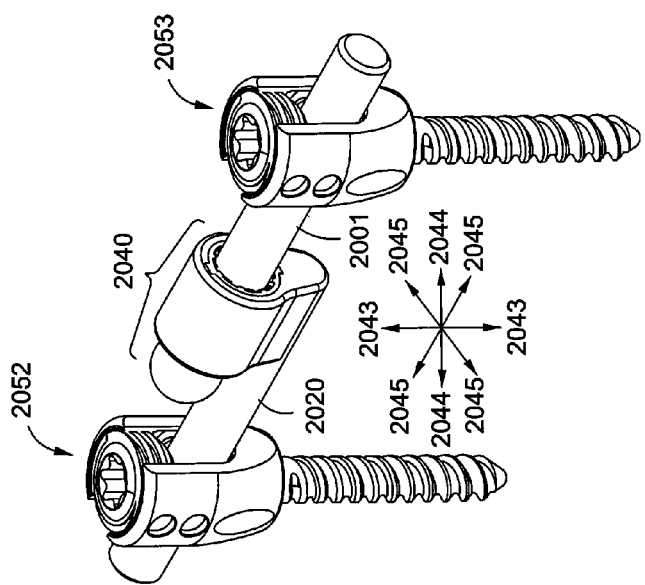
FIG. 20E

PEDICLE SCREWS AND DYNAMIC ADAPTORS

BACKGROUND

1. Field

The present invention relates generally to the field of medical devices used in posterior spinal fixation surgery, and more particularly to pedicle screws and dynamic adaptors.

2. Description of the Related Art

Posterior spinal fixation surgery is a common procedure for patients who suffer from severe spinal conditions, such as spinal displacement, spinal instability, spinal degeneration, and/or spinal stenosis. Among other therapeutic goals, a successful posterior spinal fixation surgery may lead to the stabilization and fusion of several spinal bone segments of a patient. During a posterior spinal fixation surgery, a spine surgeon may insert several pedicle screws, which may function as anchoring devices, into several spinal bone segments of the patient to establish several anchoring points. Then, the spine surgeon may engage and secure a stabilizing rod, which may be an elongated member, to the several anchoring points to restrict or limit the relative movement of the several spinal bone segments. When the posterior spinal fixation surgery is completed, the operated spinal bone segments may be substantially stabilized such that they may be in condition for spinal fusion.

Conventional pedicle screws may suffer from several drawbacks. For example, conventional pedicle screws may include components that are difficult to assembly and manipulate. In another example, conventional pedicle screws may have a high post surgical failure rate due to poor durability and low resistance to mechanical stresses. Moreover, conventional stabilizing rods may generally be made of strong and rigid materials, such that the tasks of securing and/or anchoring a conventional stabilizing rod to several non-linear anchoring points may be prohibitively difficult and time consuming.

Thus, there are needs to provide pedicle screws and dynamic adaptors with improved features and qualities.

SUMMARY

One aspect of the present invention is to provide a pedicle screw with components that may be easy to assemble and manipulate. Another aspect of the present invention is to provide a pedicle screw with better post surgical integrity and high resistance to mechanical stresses. Yet another aspect of the present invention is to provide a dynamic adaptor for flexibly connecting two stabilizing rods, which may reduce the difficulty and time for securing and anchoring the stabilizing rods to several non-linear anchoring points.

In one embodiment, the present invention may include an anchoring device which may be used in conjunction with a stabilizing rod for stabilizing one or more spinal bone segments. The anchoring device may engage a segment of the stabilizing rod and be configured to anchor the stabilizing rod to the one or more spinal bone segments. The anchoring device may have a screw having a spherical joint and a threaded shaft coupled to the spherical joint, a compression member configured to engage the spherical joint, an adaptive member configured to house the compression member and a substantial portion of the spherical joint, the adaptive member defining first and second openings and having an inner rim disposed along the second opening, the inner rim including an inner conical surface and a first pivot ring formed on the inner conical surface, the first pivot ring configured to engage the spherical joint along a circular path thereon, thereby allowing limited movement between the threaded shaft and the adaptive member while preventing the spherical joint from passing through the second opening, a cradle configured to embrace the adaptive member and reinforce the inner rim of the adaptive member, and a cap configured to engage the cradle and direct a compression force to the compression member.

In another embodiment, the present invention may include an anchoring device which may be used in conjunction with a stabilizing rod for stabilizing one or more spinal bone segments. The anchoring device may engage a segment of the stabilizing rod and be configured to anchor the stabilizing rod to the one or more spinal bone segments. The anchoring device may have a screw having a spherical joint and a threaded shaft coupled to the spherical joint, an adaptive member configured to house a substantial portion of the spherical joint, the adaptive member defining first and second openings such that the substantial portion of the spherical joint is disposed therebetween, and having a compression lock disposed adjacent to the first opening, the compression lock, when deployed, configured to engage the spherical joint and to prevent the spherical joint from passing through the first opening, a cradle configured to embrace the adaptive member and reinforce the inner rim of the adaptive member, and a cap configured to engage the cradle, thereby directing a compression force to the deployed compression lock.

In another embodiment, the present invention may include an anchoring device which may be used in conjunction with a stabilizing rod for stabilizing one or more spinal bone segments. The anchoring device is configured to anchor the stabilizing rod to the one or more spinal bone segments. The anchoring device may have a cradle having a base and a side wall coupled to the base, the base defining an opening along a plane substantially perpendicular to the side wall, the side wall having a pair of receiving ports configured to receive a portion of the stabilizing rod, a cap having first and second surfaces, the first surface configured to impart a compression force onto a first segment of the received stabilizing rod when the cap is substantially coupled to the side wall of the cradle, the second surface peripherally joining the first surface and forming an obtuse angle with the first surface, the second surface configured to contact a second segment of the received stabilizing rod when the stabilizing rod is bent around the first surface of the cap, and a screw assembly retained within the base of the cradle, and configured to receive the compression force via the stabilizing rod.

In another embodiment, the present invention may include an anchoring device which may be used for stabilizing one or more spinal bone segments, and it may be configured to anchor a stabilizing rod to the one or more spinal bone segments. The anchoring device may have a shaft having a distal end, a proximal end, a strain reliever coupled to the proximal end, and an external threaded section coupled between the strain reliever and the distal end, the external threaded section is configured to be driven into and engage one spinal bone segment, the strain reliever is configured to protect the shaft from mechanical stresses, a base member coupled to the proximal end of the shaft, the base member configured to receive a segment of the stabilizing rod, and a cap configured to assert a compression force onto the segment of the stabilizing rod when the cap is substantially coupled to the base member, thereby securing the segment of the stabilizing rod to the base member.

In another embodiment, the present invention may include a dynamic adaptor which may be used in conjunction with first and second stabilizing rods for stabilizing one or more spinal bone segments. The dynamic adaptor configured to allow a relative movement between the first and second stabilizing rods. The dynamic adaptor may have a female member coupled to the first stabilizing rod, the female member having a cylindrical socket, an insert port, and a swing port, the insert port located on a side wall of the cylindrical socket, the swing port located adjacent to the insert port, and a male member coupled to the second stabilizing rod, the male member having a joint configured to be inserted into the socket of the female member via the insert port and to be locked inside the socket when the second stabilizing rod protrude the swing port, and the joint, when locked inside the socket, having a range of rotation defined by the swing port.

In yet another embodiment, the present invention may include a dynamic adaptor, which may be used in conjunction with first and second stabilizing rods and for stabilizing one or more spinal bone segments. The dynamic adaptor may be configured to allow a relative movement between the first and second stabilizing rods. The dynamic adaptor may have a cylindrical sleeve having first and second ports, and a side wall extension formed between the first and second ports, the first and second ports configured to receive a segment of the second stabilizing rod, the side wall extension configured to be coupled to the first stabilizing rod, the cylindrical sleeve allowing the segment of the stabilizing rod to have a range of radial movement therein, the range of radial movement defining the relative movement between the first and second stabilizing rods, and a stopper configured to be coupled to the segment of the second stabilizing rod, the stopper engaging the second port of the cylindrical sleeve and configured to prevent the segment of the second stabilizing rod from leaving the first port of the cylindrical sleeve.

BRIEF DESCRIPTION OF THE DRAWINGS

Other systems, methods, features and advantages of the present invention will be or will become apparent to one with skill in the art upon examination of the following figures and detailed description. It is intended that all such additional systems, methods, features and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIGS. 1A-1D show various views of a multi-axle pedicle screw (MAPS) according to an embodiment of the present invention;

FIGS. 2A-2D show various views of the MAPS engaging a stabilizing rod according to an embodiment of the present invention;

FIG. 3A shows a cross-sectional side view of the MAPS aligning with a spinal bone segment according to an embodiment of the present invention;

FIG. 3B shows a cross-sectional side view of the MAPS being drilled into the spinal bone segment according to an embodiment of the present invention;

FIG. 3C shows a perspective view of several MAPSs anchoring the stabilizing rod to the several spinal bone segments according to an embodiment of the present invention;

FIGS. 4A-4E show various views and dimensions of a screw member according to an embodiment of the present invention;

FIGS. 6A-6C show various views of the compression member engaging the screw member according to an embodiment of the present invention;

FIGS. 7A-7F show various views and dimensions of a multifunctional adaptive member according to an embodiment of the present invention;

FIGS. 8A-8F show various views and dimensions of an alternative multifunctional adaptive member according to an embodiment of the present invention;

FIGS. 9E-9G show the cross-sectional views of the core unit having multi-axial movements according to an embodiment of the present invention;

FIGS. 12A-12C show various views of the MAPS being assembled and engaging to the stabilizing rod according to an embodiment of the present invention;

FIGS. 12D-12E show cross-sectional side views of the MAPS with a single-ring configuration according to an embodiment of the present invention;

FIGS. 12F-12G show the cross-sectional side views of the MAPS with a multiple-ring configuration according to an embodiment of the present invention;

FIGS. 13A-13B show the cross-sectional views of the stabilizing rod positioned between the cap member and the compression member according to an embodiment of the present invention;

FIGS. 14A-14E show various views and dimensions of an integrated adaptive member with a compression lock according to an embodiment of the present invention;

FIGS. 16A-16C shows various views of an integrated adaptive member with two compression locks according to an embodiment of the present invention;

FIG. 17A shows the perspective view of a core unit adopting the integrated adaptive member with one deployed compression lock according to an embodiment of the present invention;

FIG. 17B shows the perspective view of a core unit adopting the integrated adaptive member with two deployed compression locks according to an embodiment of the present invention;

FIGS. 18A-18D show various views of a dynamic screw member according to an embodiment of the present invention;

FIGS. 20A-20D show various views of an alternative dynamic adaptor according to an embodiment of the present invention; and FIGS. 20E-20G show various views of the alternative dynamic adaptor connecting two separately anchored stabilizing rods according to an embodiment of the present invention.

DETAILED DESCRIPTION

Figure 5C:
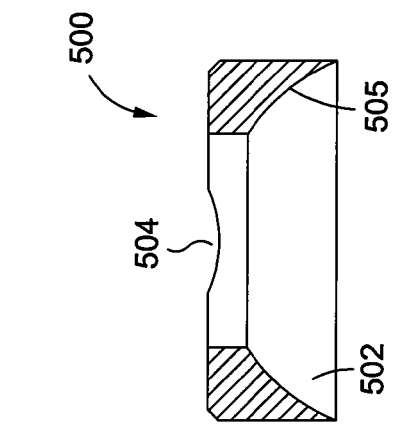
FIGS. 5A-5E show various views and dimensions of a compression member according to an embodiment of the present invention.
Figure 5E:
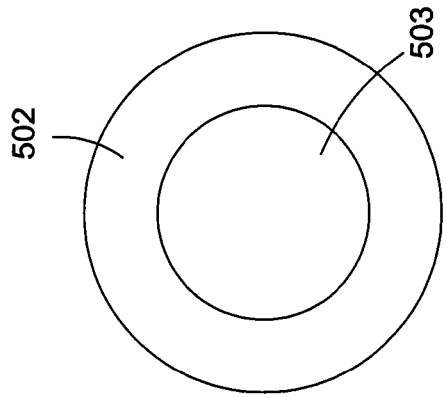
Figure 5B:
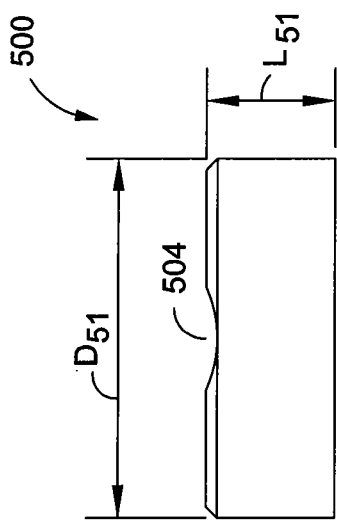
Figure 5D:
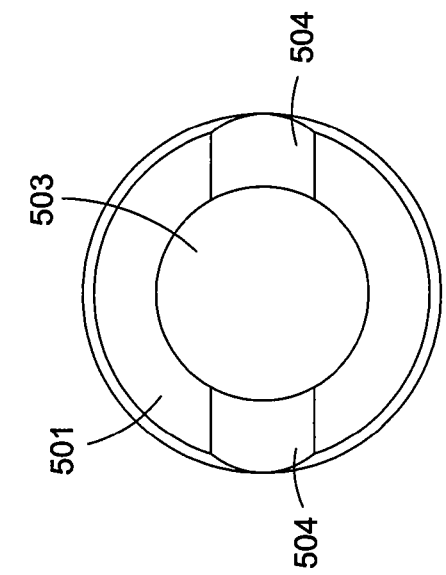
Figure 5A:
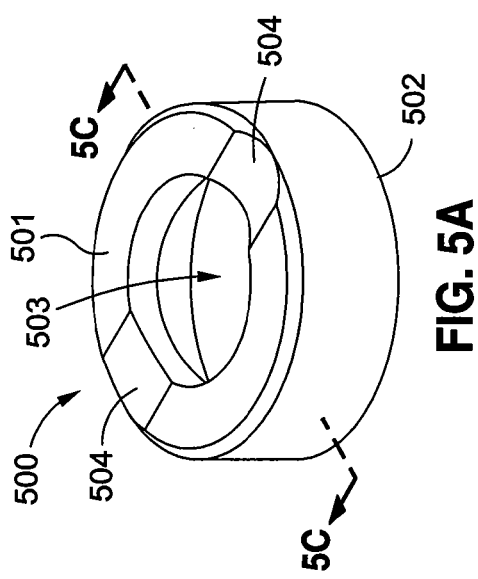

Apparatus, systems and methods that implement the embodiment of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between reference elements. In addition, the first digit of each reference number indicates the figure in which the element first appears.

FIGS. 1A-1D show a perspective view, a side view, a front view, and an expanded view of a multi-axle pedicle screw (MAPS) 100 according to an embodiment of the present invention. The MAPS 100 may include a screw member 104, a compression member 105, a multifunctional adaptive member 107, a cradle 110, and a cap 111. Generally, the screw member 104 may have a spherical joint 122 and a threaded shaft 124, so that the spherical joint 122 may provide a pivot point for the threaded shaft 124, which may be used for drilling and engaging a spinal bone segment. The compression member 105 may be placed on top of the spherical joint 122 for engaging the screw member 104.

Furthermore, the multifunctional adaptive member 107 may house the compression member 105 and a substantial portion of the spherical joint 122 to form a core unit (or screw assembly) 101. As shown in FIGS. 1A-1C, the threaded shaft 124 of the screw member 104 may protrude from the bottom of the multifunctional adaptive member 107, and it may also have a limited multi-axial movement defined by the dimensions of the multifunctional adaptive member 107. The cradle 110 may provide major structural support for the core unit 101 by substantially wrapping around a top portion of the core unit 101. As shown in FIGS. 1A-1C, threaded shaft 124 of the screw member 104 may also protrude from the bottom of the cradle 110 after the top portion of the core unit 101 is embedded inside the cradle 110 to form an open MAPS 102.

FIGS. 2A-2D show a perspective view, a side view, a front view, and an exploded view of the MAPS 100 engaging a stabilizing rod 200 according to an embodiment of the present invention. Generally, the stabilizing rod 200 may be used to stabilize several spinal bone segments by limiting the relative movement of the several spinal bone segments. In order to engage the stabilizing rod 200, the open MAPS 102 may first receive the stabilizing rod 200 via a pair of receiving ports 113 which may be part of the cradle 110. The pair of receiving ports 113 may be in any shape or form suitable for receiving the stabilizing rod 200. In one embodiment of the present invention, the pair of receiving ports 113 may be a pair of U-Shape openings as shown in FIG. 2D. In another embodiment of the present invention, the pair of receiving ports 113 may be a pair of polygonal openings, each of which may have a width greater than a diameter of the stabilizing rod 200. In yet another embodiment of the present invention, the pair of receiving ports 113 may be a pair of circular openings (not shown), each of which may have a diameter greater than the diameter of the stabilizing rod 200.

Furthermore, the compression member 105 may have a shallow trench 106 for receiving an anchored portion 201 of the stabilizing rod 200. Finally, the cap 111 may engage and secure the stabilizing rod 200 by applying a vertical compression force 130 against the anchored portion 201 of the stabilizing rod 200. In one embodiment, the cap 111 may be a set screw as shown in FIGS. 1A-1C and 2A-2C, such that the vertical compression force 130 may be produced by substantially mating an external threaded section 131 of the set screw with an internal threaded section 132 of the cradle 110. In another embodiment, the cap 111 may be a mechanical clip (not shown), such that the vertical compression force 130 may be produced by applying the mechanical clip to close the open MAPS 101. In yet another embodiment, the cap 111 may be an alternative set screw (not shown), such that the vertical compression force 130 may be produced by substantially mating an internal threaded section (not shown) of the reverse set screw with an external threaded section (not shown) of the cradle 113.

The discussion now turns to the administration of the MAPS 100 and the stabilizing rod 200. FIG. 3A shows a cross-sectional side view of the open MAPS 102 aligning with a spinal bone segment 301 according to an embodiment of the present invention. As shown in FIG. 3A, the spinal bone segment 301 may have a spinous process 311, a transverse process 312, a superior articular process 313, and a vertebral body 314. Initially, the threaded shaft 124 of the screw member 104 may be positioned at a junction between the transverse process 312 and the superior articular 313 (i.e., the pedicle area). More specifically, the threaded shaft 124 of the screw member 104 may be aligned at an insert angle $A_{31}$ from a vertical axis $A_Y$ defined by the spinous process 311. In one embodiment, the insert angle $A_{31}$ may range from about 10 degrees to about 20 degrees. The cradle 110 of the MAPS 102 may have four manipulation spots 112, such that a pair of forceps 360 may manipulate the MAPS 102 by holding the open MAPS 102 at the manipulation spots 112.

After the open MAPS 102 is properly aligned with the bone segment 301, a surgical screw driver 370 may turn the spherical joint 122 of the screw member 104 so that the threaded shaft 124 may drill into the vertebral body 314 of the spinal bone segment 301. When the threaded shaft 124 is substantially drilled into the spinal bone segment 301 as shown in FIG. 3B, the open MAPS 102 may establish an anchor point on the spinal bone segment 301. Depending on the need of a particular patient, the above procedure may be repeatedly applied to several spinal bone segments, such as spinal bone segments 301, 302, and 303. If several open MAPSs 102 are anchored to the spinal bone segments 301, 302, and 303, the stabilizing rod 200 may be used to stabilize the spinal bone segments 301, 302, and 303 by restricting their relative movement.

As shown in FIG. 3C, three MAPSs 100 may be used to anchor the stabilizing rod 200 to the spinal bone segments 301, 302, and 303. After the open MAPSs 102 establish three anchor points on the spinal bone segments 301, 302, and 303, the stabilizing rod 200 may be received by the receiving ports 113 of each open MAPS 102. To secure and anchor the stabilizing rod 200 to the spinal bone segments 301, 302, and 303, the caps 111 may be secured into the cradles 110, thereby asserting the vertical compression forces against the anchor portions 201 of the stabilizing rod 200. When all the open MAPSs 102 are closed by the caps 111, the stabilizing rod 200 may be properly anchored to the spinal bone segments 301, 302, and 303. As such, the stabilizing rod 200, along with the MAPSs 100, may function as a locking system which may stabilize the spinal bone segments by substantially restricting the relative movement thereof. Depending on the need of a particular patient, the above procedure may be repeatedly applied to different groups or sides of the spinal bone segments.

The discussion now turns to the features and dimensions of various components of the MAPS 100. FIGS. 4A-4E show a perspective view, a side view, a cross-sectional side view, a top view, and a bottom view of a screw member 400 according to an embodiment of the present invention. The screw member 400 may have a spherical joint 401, a threaded shaft 405, and a neck 404 connecting the spherical joint 401 and the threaded shaft 405. The spherical joint 401 may have a spherical joint diameter $D_{41}$, which is commonly shared by a first (top) hemispherical section 402 and a second (bottom) hemispherical section 403. In one embodiment, the spherical joint diameter $D_{41}$ may range, for example, from about 8 mm to about 9 mm. In another embodiment, the spherical joint diameter $D_{41}$ may be about 8.5 mm.

The first hemispherical section 402 may have a bearing socket 409 for receiving the surgical screw driver 370. The second hemispherical section 403 may have a flat section 410 for joining the neck 404. Although FIGS. 4A-4B show that the first hemispherical section 402 is directly connected to the second hemispherical section 403, there may be a connection member (not shown) coupled between the first and second hemispherical sections 402 and 403 according to another embodiment of the present invention. The spherical joint 402 may be a single unit such that the first hemispherical section 402 is permanently attached to the second hemispherical section 403. Alternatively, the first hemispherical section 402 may be detachable from the second hemispherical section 403.

The threaded shaft 405 may have a distal end 407 for drilling and penetrating a spinal bone segment, a proximal end 406 coupled to the neck 404, and a spiral threaded section 408 for cutting into the spinal bone segment and for engaging and anchoring the MAPS 100 to the spinal bone segment. Although FIGS. 4A-4C show that the neck 404 is attached to the second hemispherical section 403 of the spherical joint 401, the neck 404 may be detached from the second hemispherical section 403 of the spherical joint 401 according to another embodiment of the present invention. The threaded shaft 405 may have a shaft length $L_{41}$, an outer diameter $D_{42}$, and an inner diameter $D_{43}$. In one embodiment, the shaft length $L_{41}$ may range, for example, from about 25 mm to about 35 mm, the outer diameter $D_{42}$ may range, for example, from about 3 mm to about 7 mm, and the inner diameter $D_{43}$ may range, for example, from about 1.5 mm to about 2 mm. In another embodiment, the shaft length $L_{41}$ may be about 29.34 mm, the outer diameter $D_{42}$ may be about 5 mm, and the inner diameter $D_{43}$ may be about 1.7 mm.

FIGS. 5A-5E show a perspective view, a side view, a cross-sectional side view, a top view, and a bottom view of a compression member 500 according to an embodiment of the present invention. The compression member 500 may have a shape of a circular plate with an access opening 503 penetrating a first (top) surface 501 and a second (bottom) surface 502. The first surface 501 may have a shallow trench 504 for receiving the anchored portion 201 of the stabilizing rod 200 as shown in FIGS. 2A-2C. The second surface 502 may have a concave section 505 for engaging the first hemispherical section 402 of the spherical joint 401 shown in FIGS. 4A-4E. Generally, the compression member 500 may have a thickness $L_{51}$ and a compression member diameter $D_{51}$. More specifically, the compression member diameter $D_{51}$ may be smaller than the spherical joint diameter $D_{41}$ such that the compression member 500 may engage a portion of the first hemispherical section 402. In one embodiment, the thickness $L_{51}$ may range, for example, from about 2.5 mm to about 3.5 mm, and the compression member diameter $D_{51}$ may range, for example, from about 7 mm to about 9 mm. In another embodiment, the thickness $L_{51}$ may be about 2.86 mm and the compression member diameter $D_{51}$ may be about 8 mm. Moreover, in order to allow the surgical screw driver 370 to access the bearing socket 409 of the screw member 400, the access opening 503 of the compression member 500 may be wider than the bearing socket 409 of the screw member 400.

FIGS. 6A-6C show an exploded view, a perspective view and a cross-sectional side view of the compression member 500 engaging the screw member 400 according to an embodiment of the present invention. As shown in FIG. 6A, the first surface 501 of the compression member 500 may face away from the screw member 400 and the second surface 502 of the compression member 500 may be placed on top of a portion of the first hemispherical section 402 of the spherical joint 401.

As shown in FIG. 6B, the compression member 500 may lie on a horizontal plane S, which may be perpendicular to a central axis $A_{XY}$. Because the spherical joint 401 may freely rotate about the central axis $A_{XY}$, the threaded shaft 405 may have a wide range of multi-axial movements around the central axis $A_{XY}$. As shown in FIG. 6C, the second surface 502 of the compression member 500 may engage or come into contact with a part of the second hemispherical section 403 when the threaded shaft 405 moves away from the central axis $A_{XY}$.

Moreover, the access opening 503 of the compression member 500 may align with the bearing socket 409 of the screw member 400 when the threaded shaft 405 aligns with the central axis $A_{XY}$. As such, the surgical screw driver 370 may access and engage the bearing socket 409 via the access opening 503 of the compression member 500. However, when the threaded shaft 405 moves away from the central axis $A_{XY}$, the bearing socket 409 of the screw member 400 may be partially or completely blocked by the compression member 500.

FIGS. 7A-7F show a perspective view, a side view, a cross-sectional side view, an expanded view, a top view, and a bottom view of a multifunctional adaptive member 700 according to an embodiment of the present invention. Generally, the multifunctional adaptive member may have a first (top) opening 702, a second (bottom) opening 704, and a substantially cylindrical housing 701, which may have an inner surface 703 and an outer surface 705. More specifically, the multifunctional adaptive member 700 may be divided into a first (top) section 710 and a second section 720. The first section 710 may have a pair of receiving ports 716, a locking member 712, and a fastener 714.

Referring to FIG. 7A, the substantially cylindrical housing 701 may be used for shielding the compression member 500 and a substantial portion of the spherical joint 401. Accordingly, as shown in FIG. 7B, the substantially cylindrical housing 701 may have an adaptive diameter $D_{71}$ that may be greater than the spherical joint diameter $D_{41}$ and the compression member diameter $D_{51}$. In one embodiment, the adaptive diameter $D_{71}$ may range, for example, from about 8 mm to about 11 mm. In another embodiment, the adaptive diameter $D_{71}$ may be about 9.5 mm. Moreover, the substantially cylindrical housing 701 may have an adaptive height $L_{71}$. In one embodiment, the adaptive height $L_{71}$ may range, for example, from about 9 mm to about 12 mm. In another embodiment, the adaptive height $L_{71}$ may be about 9.93 mm.

Referring again to FIG. 7A, the multifunctional adaptive member 700 may have a portion of the substantially cylindrical housing 701 carved out to form the pair of receiving ports 716. The receiving ports 716 may be used for receiving the anchored portion 201 of the stabilizing rod 200. As such, the receiving ports 716 may have similar shapes and dimensions as the receiving ports 113 of the cradle 110 as shown in FIG. 2C. In one embodiment, each of the receiving ports 716 may be formed in the shape of a U and may have a port diameter $D_{72}$, which may range, for example, from about 2.5 mm to about 3.5 mm. In one embodiment, the port diameter $D_{72}$ may be about 2.83 mm.

The multifunctional adaptive member 700 may have the fastener 714 formed on the outer surface 705 of the substantially cylindrical housing 701. The fastener 714 may be used to affix and secure the multifunctional adaptive member 700 within the cradle 110 as shown in FIGS. 1A-1C. In one embodiment, the fastener 714 may be a pair of rectangular protrusions formed on the outer surface 705 of the substantially cylindrical housing 701 as shown in FIGS. 7A-7C. In another embodiment, the fastener 714 may be a pair of hemispherical bearings protruded from the outer surface 705 of the substantially cylindrical housing 701. In another embodiment, the fastener 714 may be several polygonal protrusions formed on the outer surface 705 and located on the first section 710 or the second section 720 of the multifunctional adaptive member 701. In yet another embodiment, the fasteners 714 may be a trench for receiving a protrusion formed on an inner surface (not shown) of the cradle 110.

The multifunctional adaptive member 700 may also integrate the locking member 712 to the substantially cylindrical housing 701. As shown in FIGS. 7A-7C, for example, the locking member 712 may be a pair of foldable flanges, which may be partially carved from the substantially cylindrical housing 701, and they may be located adjacent to the first opening 702 of the multifunctional adaptive member 700.

One function of the locking member 712 is to retain the compression member 500 and the substantial portion of the spherical joint 401 within the second section 720 of the multifunctional adaptive member 700. To perform this function, the locking member 712 may be deployed to partially cover an inner space of the substantially cylindrical housing 701. As a result, the first opening 702 may be partially restricted or blocked by the locking member 712 such that the compression member 500 and the spherical joint 401 may not be free to leave the second section 720 of the multifunctional adaptive member 700. In one embodiment, the locking member 712 may be a pair of foldable flanges, which may be folded upward when they are deployed as shown in FIG. 7C. In another embodiment, the locking member 712 may be a pair of foldable flanges, which may be folded downward when they are deployed. In yet another embodiment, the locking member 712 may be a single flange, which may be folded horizontally or laterally towards the inner space when they are deployed.

As shown in FIG. 7C, an inner rim 722 may be formed along the second opening 704 of the multifunctional adaptive member 700. One function of the inner rim 722 is to restrict the second opening 704 of the substantially cylindrical housing 705, such that the spherical joint 401 of the screw member 400 may be retained within the second section 720 of the multifunctional adaptive member 700. To perform this function, the inner rim 722 may have a diameter smaller than the spherical joint diameter $D_{41}$. Moreover, the inner rim 722 may also limit the multi-axial movement of the threaded shaft 405 by restricting the range of displacement of the threaded shaft neck 404. Accordingly, the range of the multi-axial movement of the threaded shaft 405 may be controlled by adjusting the diameter of the inner rim 722.

Another function of the inner rim 722 is to provide a platform for pivoting the spherical joint 401. As shown in FIG. 7D, the inner rim 722 may have an inner conical surface 724 and a pivot ring 726, which may be formed on the inner conical surface 724. Generally, the inner rim 722 may provide structural support for the pivot ring 726 via the inner conical surface 724, and the pivot ring 726 may provide a circular pivotal path for the spherical joint 401 of the screw member 400. Comparing to a contiguous contact surface or a simple conical contact surface, the pivot ring 726 may provide one or more discrete contact surfaces. Advantageously, the one or more discrete contact surfaces may provide more stable and durable pivotal support to the spherical joint 421 of the screw member 420. Furthermore, because the pivot ring 726 may be partially compressible or collapsible upon impact, it may serve as a shock absorber and substantially minimize the risk of spherical joint slippage when the stabilizing rod 200 is engaged to the MAPS 100 as shown in FIG. 3C.

In one embodiment, the pivot ring 726 may provide a circular path with a convex surface pointing towards the inner space of the substantially cylindrical housing 701. In another embodiment, the pivot ring 726 may provide a circular path with an angular surface pointing towards the inner space of the substantially cylindrical housing 701. In another embodiment, the pivot ring 726 may provide a circular path with several evenly distributed hemispherical protrusions. In yet another embodiment, the pivot ring 726 may provide a circular path with several evenly distributed pyramidal protrusions.

FIGS. 8A-8F show a perspective view, a side view, a cross-sectional front view, an expanded view, a top view, and a bottom view of an alternative multifunctional adaptive member 800 according to an embodiment of the present invention. Generally, the alternative multifunctional adaptive member 800 may be similar to the multifunctional adaptive member 700 in several ways. For example, the alternative multifunctional adaptive member 800 may have a first (top) opening 802, a second (bottom) opening 804, and a substantially cylindrical housing 801, which may have an inner surface 803 and an outer surface 805. For another example, the alternative multifunctional adaptive member 800 may be divided into a first (top) section 810 and a second section 820. The first section 810 may have a pair of receiving ports 816, a locking member 812, and a fastener 814. The second section 820 may have an inner rim 822, which may be located along the second opening 804.

Despite these similarities, the alternative multifunctional adaptive member 800 may have an alternative pivot ring 826 disposed along the inner rim 822. As shown in FIG. 8D, the inner rim 822 may have a conical surface 824, on which the pivot ring 826 may be formed. The pivot ring 826 may have a multiple-ring configuration instead of a single-ring configuration. For example, the pivot ring 826 may have two rings formed adjacent to each other. For another example, the pivot ring 826 may have a first ring 827, a second ring 828, and a third ring 838 formed adjacent to one another as shown in FIGS. 8C and 8D. For yet another example, the pivot ring 826 may have more than three rings formed on the conical surface 824. Advantageously, the multiple-ring configuration may provide additional support and impact absorption capability against the vertical compression force 130 when compared to the single-ring configuration.

In one embodiment, each of the first, second, and third rings 827, 828, and 829 may provide a circular path with a convex surface pointing towards the inner space of the substantially cylindrical housing 801. In another embodiment, each of the first, second, and third rings 827, 828, and 829 may provide a circular path with an angular surface pointing towards the inner space of the substantially cylindrical housing 801. In another embodiment, each of the first, second, and third rings 827, 828, and 829 may provide a circular path with several evenly distributed hemispherical protrusions. In yet another embodiment, each of the first, second, and third rings 827, 828, and 829 may provide a circular path with several evenly distributed pyramidal protrusions.

Figure 9D:
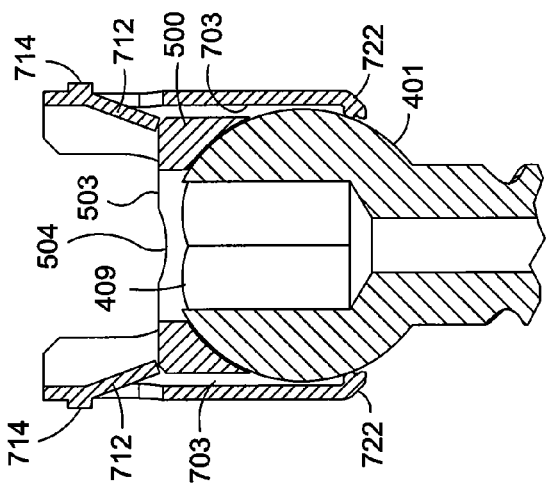
FIGS. 9A-9D show various views of a core unit according to an embodiment of the present invention.
Figure 9C:
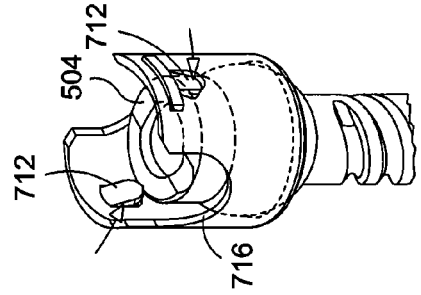
Figure 9B:
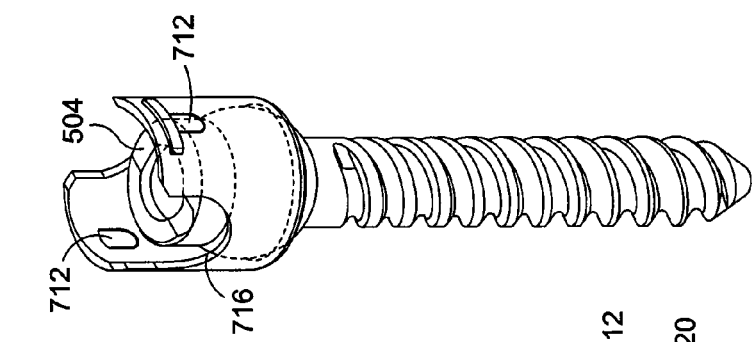
Figure 9A:
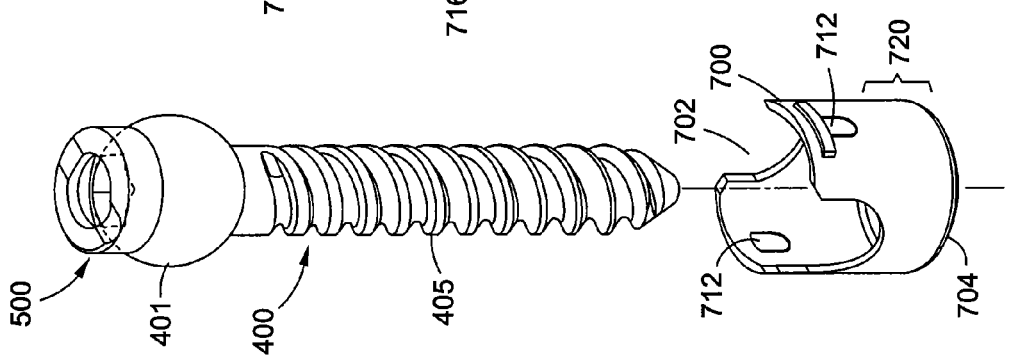

FIGS. 9A-9D show an exploded view, a perspective view, an enlarged view, and a cross-sectional view of the forming of the core unit 900 according to an embodiment of the present invention. As shown in FIG. 9A, the compression member 500 and the screw member 400 may be inserted into the multifunctional adaptive member 700 via the first opening 702 of the multifunctional adaptive member 700. Generally, the threaded shaft 405 of the screw member 400 may pass through both the first and second openings 702 and 704 of the multifunctional adaptive member 700 whereas the spherical joint 401 of the screw member 400 may be partially trapped within the second section 720 of the multifunctional adaptive member 700. More specifically, the pivot ring 726 of the inner rim 722 may engage and pivot the spherical joint 401, thereby restricting its passage across the second opening 704 of the multifunctional adaptive member 700.

After the spherical joint 401 is disposed within the second section 720 of the multifunctional adaptive member 700, the compression member 500 may be placed on top of the first hemispherical section 402 of the spherical joint 401. Particularly, the access opening 503 of the compression member 500 may align with the bearing socket 409 of the screw member 500 in order to allow the surgical screw driver 370 to access and engage the screw member 400. Moreover, the first surface 501 of the compression member 500 may be facing away from the spherical joint 401 whereas the second surface 502 of the compression member 502 may be facing toward the spherical joint 401. Furthermore, the shallow trench 504 of the compression member 500 may align with the pair of receiving ports 716 of the multifunctional adaptive member 700, so that the shallow trench 504 may form a contiguous open channel with the pair of receiving ports 716.

After the compression member 500 is aligned with the bearing socket 409 and the receiving ports 716, the locking member 712 of the multifunctional adaptive member 700 may be deployed. As shown in FIG. 9C, the locking member 712 may be a pair of flanges, which may be deployed by being folded or pressed inward. Because the deployed locking member 712 substantially restrains the upward movement of the compression member 500, the compression member 500 may not pass through the first opening 702 of the multifunctional adaptive member 700. Cooperating with the inner rim 722, the deployed locking member 712 may retain the compression member 500 and the substantial portion of the spherical joint 401 between the first and second openings 702 and 704 of the substantially cylindrical housing 701 of the multifunctional adaptive member 700.

As shown in FIG. 9D, the inner surface 703 of the substantially cylindrical housing 701 may surround the substantial portion of the spherical joint 401 without making physical contact with the spherical joint 401. As such, the multifunctional adaptive member 700 may only contact the spherical joint 401 over one or more circular paths, which may be defined by the pivot ring 726. Advantageously, this contact minimizing configuration may allow the spherical joint 401 to rotate or move more freely inside the multifunctional adaptive member 700 as the friction between the multifunctional adaptive member 700 and the spherical joint 401 may be substantially minimized. As a result, the spherical joint 401 may be less likely to be stuck at a particular position within the multifunctional adaptive member 700 before engaging and securing the stabilizing rod 200 as shown in FIG. 3C.

FIGS. 9E-9G show the cross-sectional views of the core unit 900 with a range of multi-axial movements according to an embodiment of the present invention. Initially, as shown in FIG. 9E, the core unit 900 may be resting at a stationary position when the threaded shaft 405 aligns with the central axis $A_{XY}$. At the stationary position, the surgical screw driver 370 may have full access to the bearing socket 409 of the spherical joint 401 via the access opening 503 of the compression member 500, and a circular pivotal path 910 may be located primarily on the second hemispherical section 403 of the spherical joint 401.

When the threaded shaft 405 receives a first angular force 912, it may be angularly displaced or swung to the left as shown in FIG. 9F. Depending on the size of the inner rim 722, the threaded shaft 405 may form a first multi-axial angle $A_{92}$ with the central axis $A_{XY}$. Due to the first angular force 912, the bearing socket 409 of the spherical joint 401 may rotate clockwise, and it may no longer align with the access opening 503 of the compression member 500. As such, the surgical screw driver 370 may not have access to the bearing socket 409 of the spherical joint 400 when the threaded shaft 405 is angularly displaced. Moreover, as the spherical joint 401 rotates clockwise, the pivotal circular path 910 may be shifted, such that it may be located partly on the first hemispherical section 402 and partly on the second hemispherical section 403.

Similarly, when the threaded shaft 409 receives a second angular force 914, it may be angularly displaced or swung to the right as shown in FIG. 9G. Depending on the size of the inner rim 722, the threaded shaft 405 may form a second multi-axial angle $A_{94}$ with the central axis $A_{XY}$. Due to the second angular force 912, the bearing socket 409 of the spherical joint 401 may rotate counterclockwise, and it may no longer align with the access opening 503 of the compression member 500. As such, the surgical screw driver 370 may not have access to the bearing socket 409 of the spherical joint 400 when the threaded shaft 405 is angularly displaced. Moreover, as the spherical joint 401 rotates counterclockwise, the pivotal circular path 910 may be shifted, such that it may be located partly on the first hemispherical section 402 and partly on the second hemispherical section 403. The first hemispherical section 402 may include the top half of the spherical joint 401 and the second hemispherical section 403 may include the bottom half of the spherical joint 401.

Although FIGS. 9A-9G show that the multifunctional adaptive member 700 is used to form the core unit 900, the alternative multifunctional adaptive member 800 may be used to form the core unit 900 as well according to another embodiment of the present invention. Moreover, even though FIGS. 9F-9G show that the first and second angular forces 912 and 914 are applied to the threaded shaft 405, they may be directed to the substantially cylindrical housing 701 of the multifunctional adaptive member 700 as well. More specifically, after the threaded shaft 405 is substantially drilled into a particular bone segment, it may remain substantially stationary within the particular bone segment. As a result, the first and second angular forces 912 and 914 may not be applied directly to the threaded shaft 405 of the screw member 400. Nevertheless, the threaded shaft 405 may still be angularly displaced from the central axis $A_{XY}$ because both the compression member 500 and the multifunctional adaptive member 700 may still be free to move around the spherical joint 401 of the screw member 400. Accordingly, the first and second angular forces 912 and 914 may be applied to the substantially cylindrical housing 701 of the multifunctional adaptive member 700 to produce similar multi-axial movements as shown in FIGS. 9F and 9G.

FIGS. 10A-10E show a perspective view, a side view, a cross-sectional side view, a front view, and a cross-sectional front view of a cradle 1000 according to an embodiment of the present invention. Generally, the cradle 1000 may have a side wall section 1010 and a base section 1020. In one embodiment, the cradle 1000 may have a height $L_{101}$ that may range, for example, from about 16 mm to about 19 mm. In another embodiment, the height $L_{101}$ may be about 17.85 mm. The side wall section 1010 may have a pair of receiving ports 1011, several manipulation spot 1012, an internal threaded section 1013, and a fastener 1014. In one embodiment, the side wall section 1010 may have a side wall diameter $D_{101}$ that may range, for example, from about 12 mm to about 16 mm. In another embodiment, the sidewall diameter $D_{101}$ may be about 14 mm. The base section 1020 may have a substantially cylindrical inner surface 1021, a first opening 1022, a second opening 1023, and a reinforcement member 1024. In another embodiment, the base section 1020 may have a base diameter $D_{103}$ that may range, for example, from about 10 mm to about 12 mm. In another embodiment, the base diameter $D_{103}$ may be about 11 mm.

Figure 10C:
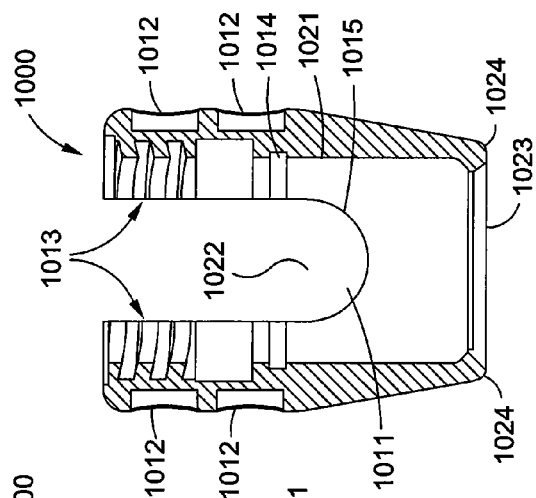
FIGS. 10A-10E show various views and dimensions of a cradle according to an embodiment of the present invention.

The pair of receiving ports 1011 may be used for receiving the anchored portion 201 of the stabilizing rod 200 as shown in FIGS. 2A-2C and 3C. More specifically, each receiving port 1011 may be an opening with a semi-circular bottom 1015 as shown in FIGS. 10B-10C. In order to properly receive the stabilizing rod 200, the semi-circular bottom 1015 may have a semi-circular diameter $D_{102}$ that is equal to or greater than the diameter of the stabilizing rod 200. In one embodiment, the semi-circular diameter $D_{102}$ may range, for example, from about 5 mm to about 6 mm. In another embodiment, the semi-circular diameter $D_{102}$ may be about 5.66 mm. The internal threaded section 1013 may be located on the inner surface of the side wall section 1010, and it may be used for engaging the set screw cap as shown in FIGS. 2A-2C and 3C. The manipulation spots 1012 may be located on the outer surface of the side wall section 1010. Advantageously, the manipulation spots 1012 may provide non-slippery and/or high friction contact surfaces for forceps 360 as shown in FIGS. 3A and 3B.

The fastener 1014 may be located on the inner surface of the side wall section 1010, and it may be used to affix and secure the core unit 900 within the base section 1020 of the cradle 1000. Generally, the fastener 1014 may be a complimentary structure of the fastener 714 (or 814) of the multifunctional adaptive member 700 (or 800). In one embodiment, the fastener 1014 may be a pair of rectangular intrusions when the fastener 714 includes a pair of rectangular protrusions. In another embodiment, the fastener 1014 may be a pair of hemispherical intrusions when the fastener 714 includes a pair of hemispherical protrusions. In another embodiment, the fastener 1014 may include polygonal intrusions. In yet another embodiment, the fastener 1014 may be a protrusion when the fastener 714 includes a trench structure.

Figure 10E:
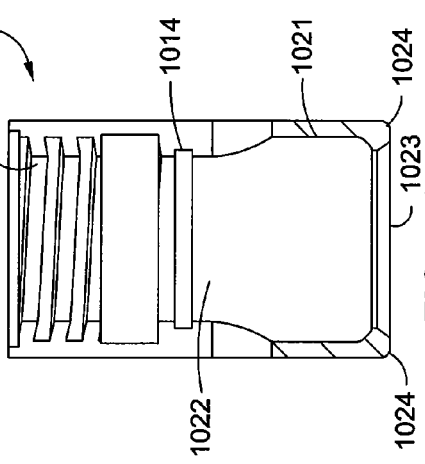
Figure 10B:
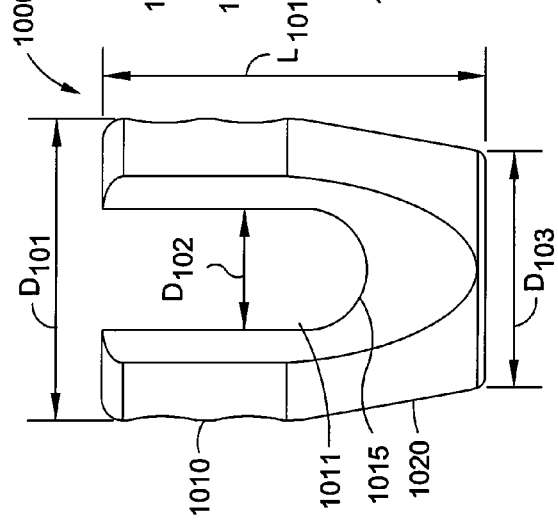
Figure 10D:
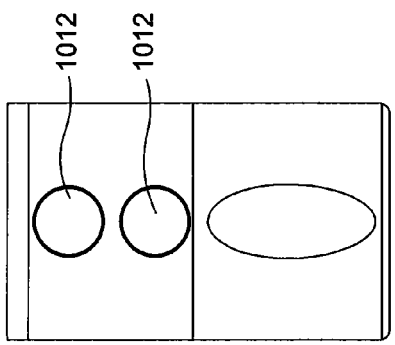
Figure 10A:
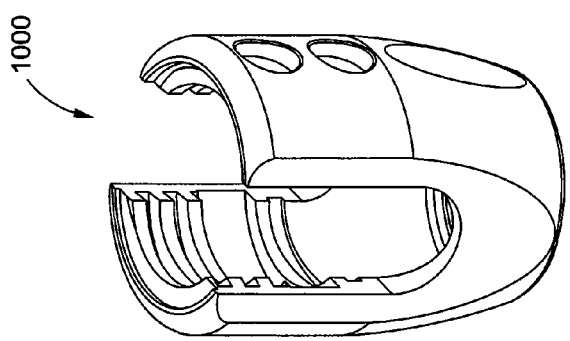

The base section 1020 of the cradle 1000 may have a substantially rectangular front surface as shown in FIGS. 10D and 10E and a substantially trapezoidal side surface as shown in FIGS. 10B and 10C. One function of the base section 1020 is to provide support and protection for the core unit 900. For example, the substantially cylindrical inner surface 1021 may protect the substantially cylindrical housing 701 of the multifunctional adaptive member 700. As another example, the reinforcement member 1024 may reinforce and support the inner rim 722 of the multifunctional adaptive member 700. Another function of the base section 1020 is to provide an anchoring interface between the core unit 900 and the stabilizing rod 200. That is, the base section 1020 may provide a platform for anchoring the stabilizing rod 200 to a spinal bone segment.

Figure 11C:
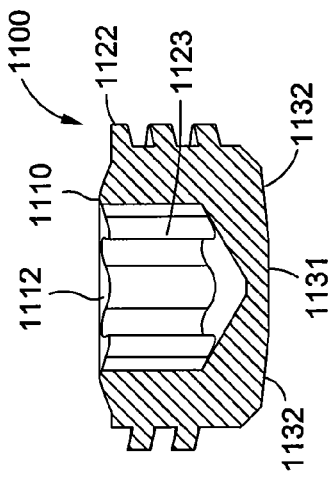
FIGS. 11A-11E show various views and dimensions of a cap member according to an embodiment of the present invention.
Figure 11E:
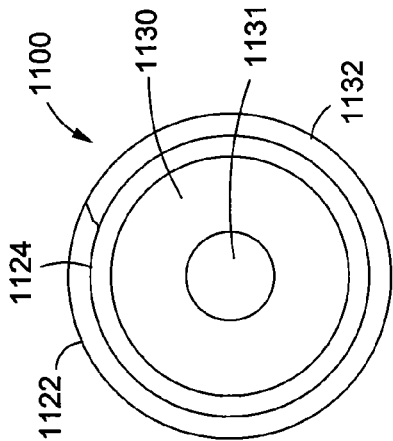
Figure 11B:
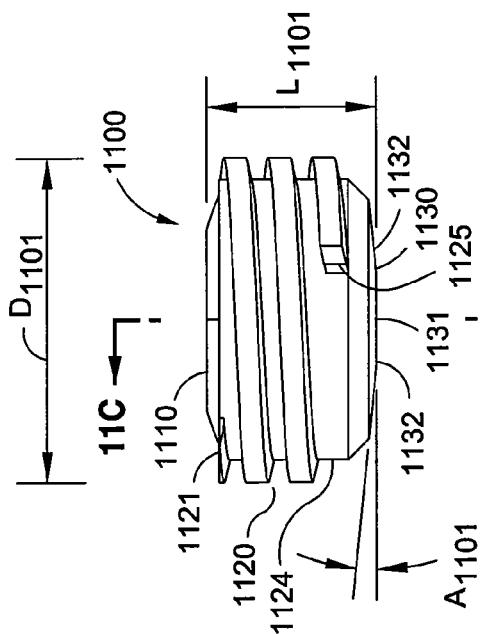
Figure 11D:
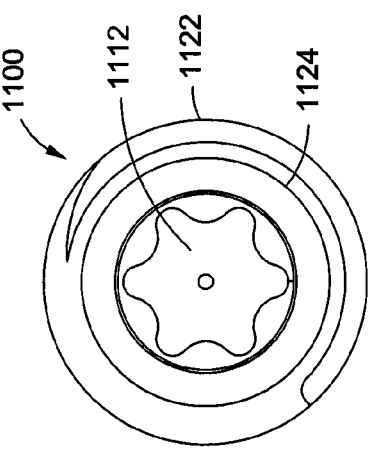
Figure 11A:
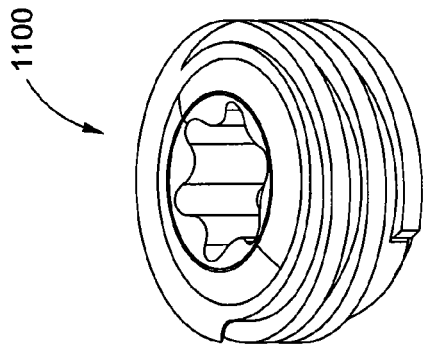
Figure 15C:
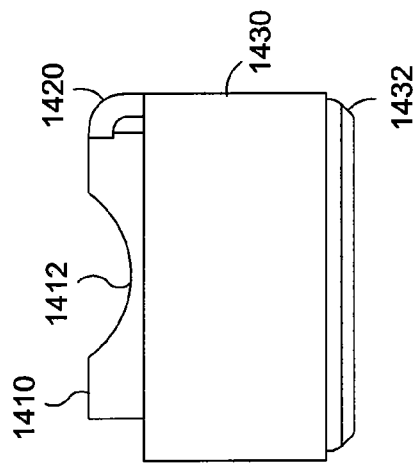
FIGS. 15A-15E show various views of the integrated adaptive member with a deployed compression lock according to an embodiment of the present invention.
Figure 15E:
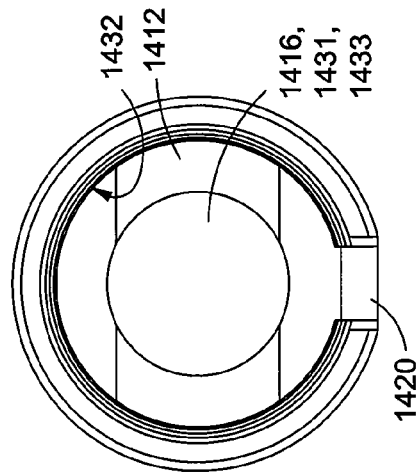
Figure 15B:
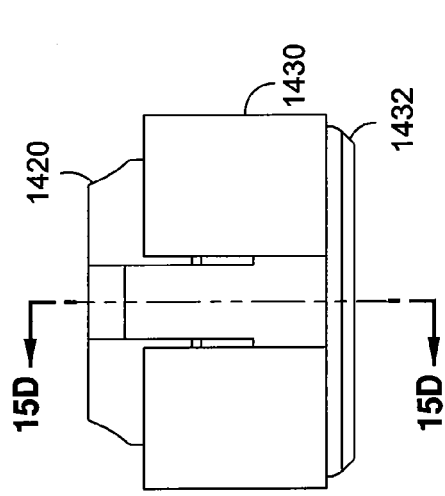
Figure 15D:
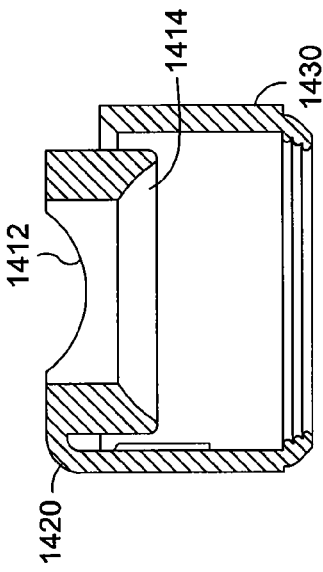
Figure 15A:
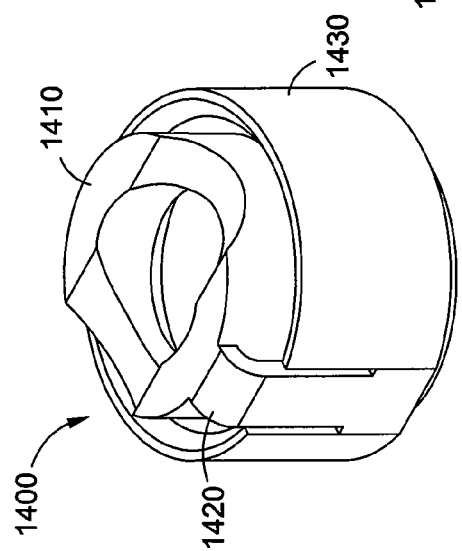

FIGS. 11A-11E show a perspective view, a side view, a cross-sectional side view, a top view, and a bottom view of a cap member 1100 according to an embodiment of the present invention. As shown in FIG. 11A, the cap member 1100 may have a first (head) section 1110, a second (neck) section 1120, and a third (bottom) section 1130. As shown in FIG. 11B, the cap member 1100 may have a cap thickness $L_{1101}$ and a cap diameter $D_{1101}$. In one embodiment, the cap thickness $L_{1101}$ may range, for example, from about 5 mm to about 7 mm, and the cap diameter $D_{1101}$ may range, for example, from about 9 mm to about 12 mm. In another embodiment, the cap thickness $L_{1101}$ may be about 5.76 mm and the cap diameter $D_{1101}$ may be about 11 mm.

The first section 1110 may have a bearing surface (or bearing head) 1112, which may extend into the second section 1120 to form a bearing socket 1123. The second section 1120 may have a cylindrical body 1124 and an external thread 1122 that may wind around the cylindrical body 1124 helicoidally. According to an embodiment of the present invention, the external thread 1122 may have a tapered head end 1121 formed adjacent to the first section 1110 and a flat tail end 1125 formed adjacent to the second section 1130 as shown in FIG. 11B. The bearing socket 1123 may engage the surgical screw driver 370 to receive an angular force. When the flat tail end 1125 of the external thread 1122 begins engaging the internal threaded section 1013 of the cradle 1000, the received angular force may be converted to a vertical compression force, which may be perpendicular to the angular force.

The third section 1130 may have a first (central) surface 1131 and a (peripheral) second surface 1132. As shown in FIG. 11E, the first surface 1131 may be located at the bottom center of the cap member 1100, and the second surface 1132 may be located peripherally around the first surface 1131. According to an embodiment of the present invention, the first surface 1131 may be a flat surface. According to another embodiment of the present invention, the first surface 1131 may be a slightly convex surface. As shown in FIG. 11B, the second surface 1132 may be a conical surface that forms an acute angle $A_{1101}$ with the first surface. In one embodiment, the acute angle $A_{1101}$ may range, for example, from 3 degrees to about 8 degrees. In another embodiment, the acute angle $A_{1101}$ may be about 5.81 degrees.

The discussion now turns to the assembling and administration of the MAPS. Referring to FIG. 12A, the open MAPS 1210 may be assembled by inserting the core unit 900 as shown in FIG. 9C into the cradle 1000 as shown in FIGS. 10A-10E. When the fastener 714 of the multifunctional adaptor 700 engages the fastener 1014 of the cradle 1000, the core unit 900 may be properly affixed and secured within the base section 1020 of the cradle 1000. As a result of the proper affixing, the pair of receiving ports 716 of the multifunctional adaptive member 700 may align with the pair of receiving ports 1011 of the cradle 1000. Accordingly, the shallow trench 504 may form a contiguous open channel with the receiving ports 716 and 1011. Furthermore, the threaded shaft 405 of the screw member 400 may protrude from the second opening 1023 thereof.

After being assembled, the MAPS 1210 may be ready for use. Specifically, the MAPS 1210 may be administered to a particular spinal bone segment by driving the threaded shaft 405 into spinal bone segment. At the initial stage, the threaded shaft 405 may align with the central axis $A_{XY}$, such that the access opening 503 of the compression member 500 may align with the bearing socket 409 of the spherical joint 401. Accordingly, the surgical screw driver 370 may access and engage the bearing socket 409 and drive the threaded shaft 405 into the spinal bone segment to establish an anchor point.

Referring to FIG. 12B, the anchored portion 201 of the stabilizing rod 200 may be placed between the receiving ports 716 and between the receiving ports 1011 after the open MAPS 1210 establishes the anchor point on the spinal bone segment. As a result, the anchored segment 201 of the stabilizing rod 200 may rest on the shallow trench 504 of the compression member 500.

If the stabilizing rod 200 is to be received by more than one open MAPS 1210, it is possible that the stabilizing rod 200 may not be properly aligned with the receiving ports 716 and 1011 initially because the several open MAPS 1210 may have a non-linear distribution. In order to overcome the problem caused by the non-linear distribution of the open MAPS 1210, the cradle 700, along with the multifunctional adaptive member 700 and the compression member 500, of each open MAPS 1210 may be adjusted by rotating around the respective spherical joint 401. Accordingly, the threaded shaft 405 of each open MAPS 1210 may be angularly displaced from the respective central axis $A_{XY}$.

After the stabilizing rod 200 is properly received by the open MAPS 1210, the cap member 1100 may be used to close the open MAPS 1210. As the cap member 1100 is substantially coupled to the open MAPS 1210, the cap member 1100 may direct a vertical compression force 1214 to the anchored segment 201 of the stabilizing rod 200. In return, the anchored segment 201 of the stabilizing rod 200 may redirect the compression force 1215 to the compression member 500, which may further cause the spherical joint 401 to redirect the compression force 1214 to the pivot ring 726 (or 826) of the multifunctional adaptive member 700 (or 800).

Referring to FIGS. 12D and 12E, which show a cross-sectional side view of the MAPS 1220, the spherical joint 401 may redirect the compression force 1214 to the convex surface of the pivot ring 726. As a result, the convex surface of the pivot ring 726 may be partially compressed or collapsed. The partially collapsed pivot ring 726 may assert an increased amount of friction against the surface of the spherical joint 401, thereby substantially reducing the range of movement of the spherical joint 401 in relative to the multifunctional adaptive member 700. Subsequently, the reinforcement member 1024 of the cradle 1000 may provide structural support and reinforcement to the inner rim 722 of the multifunctional adaptive member 700, thereby asserting a reaction force 1216 against the surface of the spherical joint 401.

Consequentially, the reaction force 1216 may balance the compression force 1214 to substantially stabilize the spherical joint 401 within the substantially cylindrical housing 701 of the multifunctional adaptive member 700. Advantageously, the partially collapsed pivot ring 726 may enhance the stabilization of the spherical joint 401 by absorbing the initial impact or shock caused by the compression force 1214. Consequentially, the compression force 1214 may cooperate with the reaction force 1216 to lock the spherical joint 401 in a particular position within the multifunctional adaptive member 700 and thus prevent the spherical joint 401 from further rotating. At the locked stage, the multi-axial movement of the threaded shaft 405 may be substantially reduced and restrained.

Referring to FIGS. 12F and 12G, which shows a cross-sectional side view of the MAPS 1230 with the alternative multifunctional adaptive member 800, the spherical joint 401 may redirect the compression force 1214 to the convex surface of the pivot ring 826. As a result, the second ring 828 of the pivot ring 826 may be partially compressed or collapsed. The partially collapsed second ring 828 may assert an increased amount of friction against the surface of the spherical joint 401, thereby substantially reducing the range of movement of the spherical joint 401 relative to the multifunctional adaptive member 800. Subsequently, the reinforcement member 1024 of the cradle 1000 may provide structural support and reinforcement to the inner rim 822 of the multifunctional adaptive member 800. As a result, the pivot ring 826 may receive the reaction force 1216 from the reinforcement member 1024 and redirect it as a series of reaction forces 1217 against the surface of the spherical joint 401 via the first, second and third rings 827, 828, and 829.

Consequentially, the series of reaction forces 1217 may balance the compression force 1214 to substantially stabilize the spherical joint 401 within the substantially cylindrical housing 801 of the multifunctional adaptive member 800. Because the series of reaction forces 1217 are more spread out than the reaction force 1216 as shown in FIG. 12E, the multiple ring configuration may provide more stability than the single-ring configuration. Advantageously, the partially collapsed second ring 828 may further enhance the stabilization of the spherical joint 401 by absorbing the initial impact or shock caused by the compression force 1214 while the first and third rings 827 and 829 may hold the spherical joint 401 in place and prevent the spherical joint 401 from any slippery motion around the pivot ring 826. As a result, the compression force 1214 may cooperate with the reaction force 1216 to lock the spherical joint 401 in a particular position within the multifunctional adaptive member 800 and thus prevent the spherical joint 401 from further rotating. At the locked stage, the multi-axial movement of the threaded shaft 405 may be substantially reduced and restrained.

FIGS. 13A-13B show the cross-sectional views of the stabilizing rod 200 positioned between the cap member 1100 and the compression member 500 according to an embodiment of the present invention. As shown in FIG. 13A, the stabilizing rod 200 may be at resting position when the stabilizing rod 200 is not substantially stressed. At the resting position, the anchored portion 201 of the stabilizing rod may contact the first surface 1131 of the cap member 1100 without contacting the second surface 1132 of the cap member 1100.

As shown in FIG. 13B, the stabilizing rod 200 may receive a first stress 1302 and a second stress 1304 after it is anchored to a particular spinal bone segment. Mainly, the first and second stresses 1302 and 1304 may be caused by a relative movement of a group of adjacent spinal bone segments which may be anchored by the anchored segment 201 of the stabilizing rod 200. Because the second surface 1132 of the cap member 1100 may slightly incline from the first surface 1131 of the cap member 1100, the third (bottom) section 1130 of the cap member 1100 may allow the anchored segment 201 of the stabilizing rod 200 to bend slightly towards the cap member 1100.

As a result, the stabilizing rod 200 may redirect the first and second stresses 1302 and 1304 to the second surface 1132 of the cap member 1100. By virtue of redirecting the first and second stresses 1302 and 1304, the stabilizing rod 200 may allow a limited range of movement among the group of adjacent spinal bone segments while stabilizing them. Furthermore, the inclined second surface 1132 may perform as a buffer segment to avoid abrupt contact between the edge of the cap member 1100 and the anchored segment 201 of the stabilizing rod 200. Advantageously, the inclined second surface 1132 may help reduce a risk of overstraining or breaking the stabilizing rod 200.

Although FIGS. 13A and 13B show that the first and second stresses 1302 and 1304 are pointing away from the anchored point, the first and second stresses 1302 and 1304 may be pointing toward the anchored point as well. Similar to the inclined second surface 1132 of the cap member 1100, the shallow trench 504 of the compression member 500 may slightly curve away from the anchored point (not shown) according to an embodiment of the present invention. The slightly curved shallow trench 504 may serve similar functions as the second surface 1132 of the cap member 1100. For example, the slightly curved shallow trench 504 may allow the anchored segment 201 of the stabilizing rod 200 to redirect the first and second stresses 1302 and 1304, and thereby allowing the limited range of movement among the group of adjacent spinal bone segments. For another example, the slightly curved shallow trench 504 may perform as a buffer segment to avoid abrupt contact between the edge of the compression member 500 and the anchored segment 201 of the stabilizing rod 200. Advantageously, the slightly curved shallow trench 504 may help reduce a risk of overstraining or breaking the stabilizing rod 200.

The discussion now turns to an integrated adaptive member. FIGS. 14A-14E show a perspective view, a front view, a side view, a cross-sectional side view, and an enlarged view of an integrated adaptive member 1400 with a compression lock 1410 according to an embodiment of the present invention. The integrated adaptive member 1400 may include similar structural and functional features as the multifunctional adaptive member 700 and the alternative multifunctional adaptive member 800. For example, the integrated adaptive member 1400 may include a first opening 1431, a second opening 1433, and a substantially cylindrical housing 1430 formed between the first and second openings 1431 and 1433. Particularly, the substantially cylindrical housing 1430 may be used for housing the substantial portion of the spherical joint 401, and the second opening 1433 may allow the threaded shaft 405 of the screw member 400 to pass through the substantially cylindrical housing 1430.

Furthermore, the integrated adaptive member 1400 may include an inner rim 1432 formed along the second opening 1433. The inner rim 1432 may have a conical surface 1434 and a pivot ring 1436 formed thereon. Generally, the pivot ring 1436 may include structural and functional features similar to those of the pivot rings 726 and 826 as discussed in FIGS. 7A-7F, 8A-8F, 9A-9E, and 12A-12G. In one embodiment of the present invention, the pivot ring 1436 may have a multiple ring structure as shown in FIGS. 14D and 14E. For example, the pivot ring 1436 may include a first ring 1437, a second ring 1438, and a third ring 1439. In another embodiment of the present invention, the pivot ring 1436 may have a single-ring structure like the pivot ring 726 as shown in FIGS. 7A-7F.

Despite the above stated similarity, the integrated adaptive member 1400 may be different from the multifunctional adaptive member 700 and/or the alternative multifunctional adaptive member 800 in at least one aspect. Mainly, the integrated adaptive member 1400 may include a compression lock 1410, which may integrate and incorporate the structural and functional features of the compression member 500 and the locking members 712 and 812. Such integration may be advantageous because it may reduce the amount of components and number of steps for assembling the MAPS 100. Particularly, the compression lock 1410 may include a compression member 1411 and a hinge lock 1418.

Like the compression member 500, the compression member 1411 may have a shallow trench 1412 for receiving and engaging the stabilizing rod 200, an access opening 1416 for accessing the bearing socket 409 of the screw member 400, and a substantially concave surface 1414 for engaging the spherical joint 401 of the screw member 400. Unlike the compression member 500, which may be a separate component of the substantially cylindrical housing 701 (or 801), the compression member 1410 may be an integrated part of the substantially cylindrical housing 1430 as it may be connected thereto via the hinge lock 1418.

The hinge lock 1418 may be formed adjacent to the first opening 1431 of the integrated adaptive member 1400. Before the hinge lock 1418 is deployed, the first opening 1431 of the integrated adaptive member 1400 may be substantially unrestricted, such that the inner space surrounded by the substantially cylindrical housing 1430 may be fully accessible. Accordingly, the screw member 400 may be inserted into the substantially cylindrical housing 1430 when the hinge lock 1418 is at the un-deployed position. Although FIGS. 14A-14E show that the compression member 1411 is substantially orthogonal to the first opening 1431 of the integrated adaptive member 1400 when the hinge lock 1418 is at the un-deployed position, the compression member 1411 may have other spatial relationships with the first opening 1431 according to various embodiments of the present invention. For example, the compression member 1411 may form an obtuse angle, as opposed to a right angle, with the first opening 1431 when the hinge lock 1418 is not yet deployed. For another example, the compression member 1411 may be parallel to, but without overlapping, the first opening 1431 when the hinge lock 1418 is not yet deployed.

Referring to FIGS. 15A-15E, which show a perspective view, a back view, a side view, a cross-sectional side view, and a top view of the integrated adaptive member 1400 with the hinge lock 1418 deployed, the compression member 1411 may substantially cover or restrict the first opening 1431. Consequentially, the compression member 1411, along with the deployed hinge lock 1418, may prevent the spherical joint 401 from passing through the first opening 1431 of the integrated adaptive member 1400. Although FIGS. 14A-14E and 15A-15E show that the hinge lock 1418 is a single-piece flexible component, which may be foldable along the first opening 1431 of the integrated adaptive member 1400, the hinge lock 1418 may be a multiple-piece mechanical joint according to another embodiment of the present invention.

FIGS. 16A-16C show various views of an integrated adaptive member 1600 with two compression locks 1610 and 1620 according to an embodiment of the present invention. The integrated adaptive member 1600 may be similar to the integrated adaptive member 1400 in several aspects. For example, the integrated adaptive member 1600 may include a first opening 1631, a second opening 1633, and a substantially cylindrical housing 1630 formed between the first and second openings 1631 and 1633. Particularly, the substantially cylindrical housing 1630 may be used for housing the substantial portion of the spherical joint 401, and the second opening 1633 may allow the threaded shaft 405 of the screw member 400 to pass through the substantially cylindrical housing 1630. For another example, the integrated adaptive member 1600 may incorporate the structural and functional features of the substantially cylindrical housing 1630.

For yet another example, the integrated adaptive member 1600 may include an inner rim 1632 formed along the second opening 1633. The inner rim 1632 may have a conical surface 1634 and a pivot ring 1636 formed on the conical surface 1634. Generally, the pivot ring 1636 may include structural and functional features similar to those of the pivot rings 726 and 826 as discussed in FIGS. 7A-7F, 8A-8F, 9A-9E, and 12A-12G. In one embodiment of the present invention, the pivot ring 1636 may have a multiple ring structure as shown in FIGS. 14D and 14E, which may include a first ring 1637, a second ring 1638, and a third ring 1639. In another embodiment of the present invention, the pivot ring 1636 may have a single-ring structure like the pivot ring 726 as shown in FIGS. 7A-7F.

Despite the above stated similarities, the integrated adaptive member 1600 may be different from the integrated adaptive member 1400 in at least one aspect. For example, the integrated adaptive member 1600 may have a pair of compression locks 1610 and 1620 instead of a single compression lock 1410. As shown in FIGS. 16A-16C, the dual (first and second) compression locks 1610 and 1620 may include the respective (first and second) compression members 1611 and 1621 and the respective (first and second) hinge locks 1618 and 1628. The first compression member 1611 may have a first inner arc 1612, and it may be connected to the substantially cylindrical housing 1630 at a first end position 1601 via the first hinge lock 1618. Similarly, the second compression member 1621 may have a second inner arc 1622, and it may be connected to the substantially cylindrical housing 1630 at a second end position 1602 via the second hinge lock 1618.

After the screw member 400 is properly inserted into the integrated adaptive member 1600, the first and second hinge locks 1618 and 1628 may be deployed. When both the first and second hinge locks 1618 and 1628 are deployed, the first and second compression members 1611 and 1621 may be folded downward to restrict the first opening 1601 of the integrated adaptive member 1600. Consequentially, the substantial portion of the spherical joint 401 may not be free to leave the substantially cylindrical housing 1630. At their deployed states, the first and second inner arcs 1612 and 1622 of the first and second compression members 1611 and 1621 may combine to form an access opening 1640, which may allow access to the bearing socket 409 of the screw member 400.

Because of the additional compression lock, the integrated adaptive member 1600 may require additional manufacturing and/or assembling processes when compared to the integrated adaptive member 1400. Nevertheless, the additional compression lock may provide a more evenly distributed support system for the stabilizing rod 200 and the compression force imparted by the cap member 1100. Advantageously, the duel compression lock configuration of the integrated adaptive member 1600 may be more durable and less susceptible to breakage when compared to the single compression lock configuration of the integrated adaptive member 1400.

Both the integrated adaptive member 1400 and 1600 may be combined with the screw member 400 to form a core unit similar to the core unit 900 as described in FIGS. 9A-9E. For example, as shown in FIG. 17A, a core unit 1710 may include the screw member 400 and the integrated adaptive member 1400 with a deployed compression lock 1410 according to an embodiment of the present invention. For another example, as shown in FIG. 17B, a core unit 1720 may include the screw member 400 and the integrated adaptive member 1600 with two deployed compression locks 1610 and 1620 according to another embodiment of the present invention. Consequentially, both the core units 1710 and 1720 may be inserted into and secured within the cradle 1000 to form the open MAPS 1210.

The discussion now turns to a dynamic screw member, which may be interchangeable with the screw member 400 in forming the MAPS. FIGS. 18A-18D show a perspective view, a side view, a cross-sectional side view, and an expanded view of a dynamic screw member 1800 according to an alternative embodiment of the present invention. The dynamic screw member 1800 may be similar to the screw member 400 in many aspects. For example, the dynamic screw member 1800 may have a spherical joint 1810 and a threaded shaft 1820. For another example, the spherical joint 1810 may have a bearing socket 1819, a first hemispherical section 1812, and a second hemispherical section 1814. For yet another example, the threaded shaft 1820 may have a proximal end 1821, a distal end 1826, a neck 1822, and an external threaded section 1824. More specifically, the distal end 1826 may have a pointy head for breaking open the spinal bone segment, and the external threaded section 1824 may be used for driving into and engaging the spinal bone segment.

Despite the above stated similarities, the dynamic screw member 1800 may be different from the screw member 400 in at least one aspect. Mainly, the dynamic screw member 1800 may include a strain reliever 1823 to protect the threaded shaft 1820 from mechanical stresses. As shown in FIGS. 18A-18D, the strain reliever 1823 may be formed on the neck 1822, which may be located between the spherical joint 1810 and the external threaded section 1824.

During the regular course of use, the compression force and/or the relative movement among the spinal bone segments may produce a series of mechanical stresses 1821 and 1832. As shown in FIG. 18B, the mechanical stresses 1831 and 1832 may be directed to the spherical joint 1810. Because the external threaded section 1824 may be deeply anchored to the spinal bone segment, it may be relatively immobile and therefore insensitive to the mechanical stresses 1831 and 1832. Consequentially, the mechanical stresses 1831 and 1832 may laterally displace the spherical joint 1810, thereby causing the neck 1822 to bend away from the shaft axle $A_S$.

Without the strain reliever 1823, the neck 1822 may be susceptible to deformation and/or breakage when it is substantially bent away from the shaft axle $A_S$. This is mainly due to the fact that the threaded shaft 1820 is made of material that may be rigid, inflexible or even brittle. In order to release or relieve the stress endured by the neck 1822, the strain reliever 1823 may be formed thereon to allow the outer region of the neck 1822 to be more flexible and thus less susceptible to deformation or breakage. As shown in FIGS. 18A-18D, a series of helical slits 1825 may be carved into the outer region of the neck 1822 to form an outer compression region 1840. These helical slits 1825 may create space and discontinuity for the outer compression region 1840, such that the neck 1822 may be partially and temporarily stretched and/or compressed when the mechanical stresses 1811 and 1812 are directed to the spherical joint 1810.

As shown in FIG. 18D, each of the helical slits 1827 and 1829 may have a slit compression angle $A_{181}$, the degrees of which may depend on the width of the helical slit 1825. When a first mechanical stress 1832 is directed to the spherical joint 1810, the helical slits 1827 may become narrower while the helical slits 1829 may become wider. As a result, the outer compressible region 1842 may be stretched while the outer compressible region 1841 may be compressed by a total compression angle $A_{182}$. Similarly, when a second mechanical stress 1831 is directed to the spherical joint 1810, the helical slits 1829 may become narrower while the helical slits 1827 may become wider. As a result, the outer compressible region 1841 may be stretched while the outer compressible region 1842 may be compressed by a total compression angle $A_{184}$.

Generally, the total compression angles $A_{182}$ and $A_{184}$ may be directly proportional to the number of helical slits 1827 and 1829 and the slit compression angle $A_{181}$. Although FIGS. 16A-16D show that the strain reliever 1823 is actuated by using the helical slits 1825, other compressible devices or structures may be used to actuate the strain reliever 1823. For example, a series of evenly distributed horizontal slits may be used to actuate the strain reliever 1823 in one embodiment of the present invention. For another example, a series of densely distributed horizontal slits and a series of sparsely distributed horizontal slits may be used to actuate the strain reliever 1823 in another embodiment of the present invention. For yet another example, a flexible material may be used to form the outer compressible region 1840 in yet another embodiment of the present invention.

Although it is desirable that the neck 1822 may afford a certain degree of flexibility, it is worth nothing that such flexibility should not be overextended because it may reduce the stabilizing rod's ability to stabilize the spinal bone segments. As such, the total compression angles $A_{182}$ and $A_{184}$ may have an optimal range. In one embodiment, the optimal range may start, for example, from about 0 degree to about 20 degrees. In another embodiment, the optimal range may start, for example, from about 0.5 degree to about 10 degrees. In yet another embodiment, the optimal range may start, for example, from about 1 degree to about 5 degrees.

The discussion now turns to a dynamic adaptor for connecting two stabilizing rods, each of which may be anchored to two spinal bone segments by two MAPS. Conventionally, a straight stabilizing rod may be anchored to two spinal bone segments by two pedicle screws. The straight stabilizing rod may be reshaped to conform to the contour of a particular section of spinal bone segments. However, the reshaping of the straight stabilizing rod may require lengthy procedures and extra surgical equipment because the stabilizing rod may generally be made of sturdy materials which are hard to bend. To improve the maneuverability of the conventional stabilizing rod and the conventional techniques for reshaping the stabilizing rod, various embodiments of the present invention may include a dynamic adaptor for connecting two separately anchored stabilizing rods and for allowing a limited range of movement between the two separately anchored stabilizing rods.

Figure 19B:
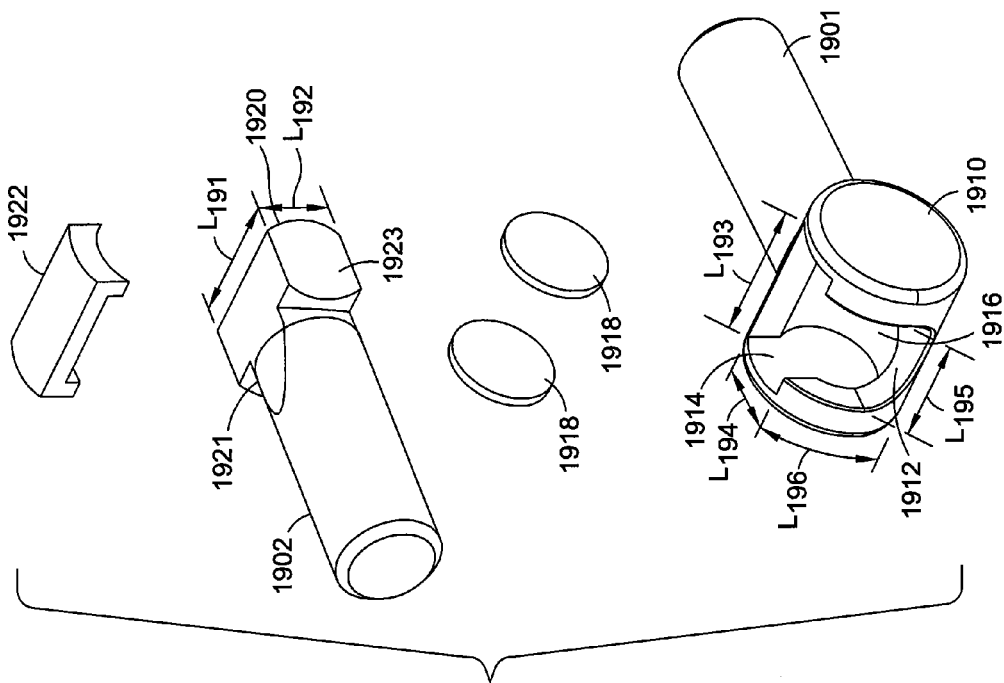
FIGS. 19A-19G show various views of a dynamic adaptor coupled between two stabilizing rods according to an embodiment of the present invention.
Figure 19A:
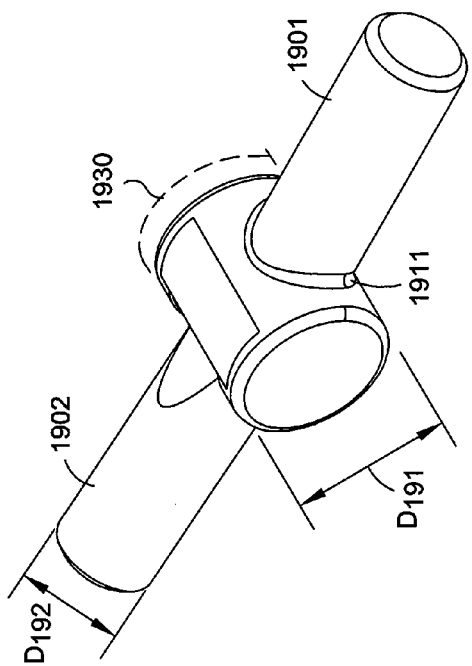
Figure 19C:
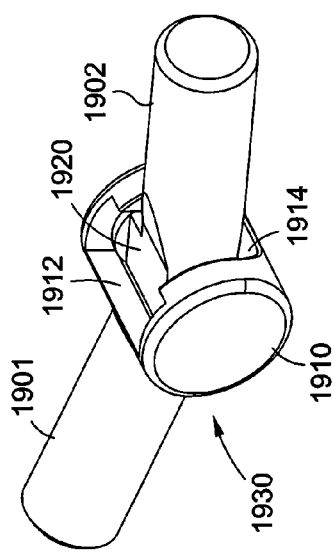
Figure 19E:
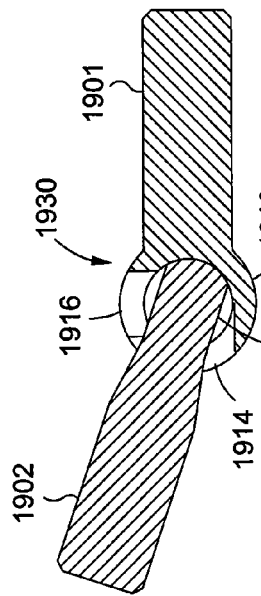
Figure 19G:
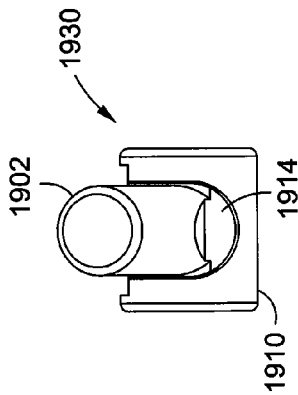
Figure 19D:
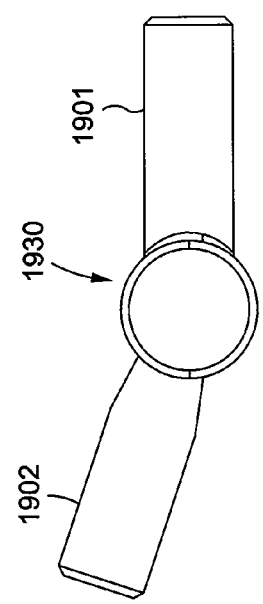

FIGS. 19A-19G show a perspective view, an exploded view, a side view, a cross-sectional side view, a top view, and a bottom view of a dynamic adaptor 1930 connecting a first stabilizing rod 1901 and a second stabilizing rod 1902. The dynamic adaptor 1930 may include a female member 1910 and a male member 1920. As shown in FIG. 19A, the first and second stabilizing rods 1901 and 1902 may each have a rod diameter $D_{192}$, and the dynamic adaptor 1930 may have a dynamic adaptor diameter $D_{191}$. In one embodiment, the rod diameter $D_{192}$ may range, for example, from about 4 mm to about 7 mm, and the dynamic adaptor diameter $D_{191}$ may range, for example, from about 7 mm to about 10 mm. In another embodiment, the rod diameter $D_{192}$ may be about 5.5 mm and the dynamic adaptor diameter $D_{191}$ may be about 8.5 mm.

Generally, the female member 1910 may be coupled to the first stabilizing rod 1901, and the male member 1920 may be coupled to the second stabilizing rod 1902. Depending on the design goal, the female and male members 1910 and 1920 may or may not be permanently attached to the first and second stabilizing rods 1901 and 1902. In one embodiment, the female member 1910 may be connectable to the first elongated member 1901 via a female connection port 1911, and the male member 1920 may be connectable to the second elongated member 1902 via a male connection port 1921. In another embodiment, the female member 1910 may be formed on an end of the first elongated member 1901, and the male member 1920 may be formed on an end of the second elongated member 1902.

As shown in FIG. 19B, the female member 1910 may include a cylindrical socket 1916, an insert port 1914 formed on the side of the cylindrical socket 1916, and a swing port 1912 formed adjacent to the insert port 1914. The male member 1920 may include a joint 1923 and a locking piece 1922. To form the dynamic adaptor 1930, the joint 1923 of the male member 1920 may be inserted into the cylindrical socket 1916 of the female member 1910 via the insert port 1914. According to an embodiment of the present invention, the joint 1923 may have a joint height $L_{191}$ and a joint width $L_{192}$, while the insert port 1914 may have an insert port height $L_{193}$ and an insert port width $L_{194}$. To properly receive the joint 1923, the insert port height $L_{193}$ may be greater than the joint height $L_{191}$ and insert port width $L_{194}$ may be greater than the joint width $L_{192}$.

After the joint 1923 is inserted into the cylindrical socket 1916, the second stabilizing rod 1902 may protrude directly from the insert port 1914. In order to lock the joint 1923 within the cylindrical socket 1916, the joint 1923 may be rotated toward the swing port 1912, such that the second stabilizing rod 1902 may protrude directly from the swing port 1912. According to an embodiment of the present invention, the swing port 1912 may have a swing port height $L_{195}$ and a swing port width $L_{196}$. For preventing the joint 1923 from leaving the cylindrical socket 1916, the swing port height $L_{195}$ may generally be smaller than the joint height $L_{191}$.

After the second stabilizing rod 1902 is radially aligned with the swing port 1912 as shown in FIGS. 19C-19F, the locking piece 1922 may be placed on top of the insert port 1914. Consequentially, the insert port 1914 may be substantially sealed and the second stabilizing rod 1902 may be blocked from returning to the original insertion position. Advantageously, the second stabilizing rod 1902 may still be able to move within the boundary of the swing port 1912. For allowing the second stabilizing rod 1902 to have a limited lateral movement along the swing port height $L_{195}$ direction, the swing port height $L_{195}$ may generally be slightly greater than the rod diameter $D_{192}$. Moreover, the magnitude of the swing port width $L_{196}$ may define a range of rotation of the joint 1923, which may further define the relative movement between the first and second stabilizing rods 1901 and 1902.

Figure 19F:
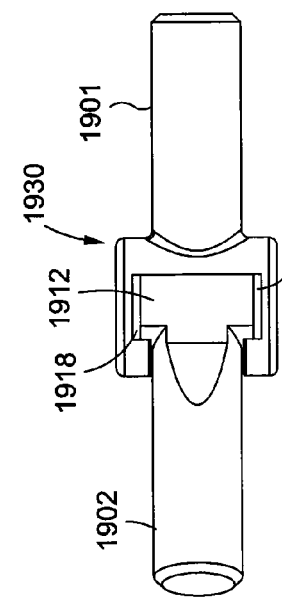

A pair of spacer discs 1918 may be inserted between the joint 1923 and the cylindrical socket 1916 as shown in FIGS. 19B and 19F. The pair of spacer discs 1918 may be used for stabilizing the joint 1923 within the cylindrical socket 1916 and for absorbing shock and/or stress associated with the limited lateral movement of the second stabilizing rod 1902. The pair of spacer 1918 may be made of any type of shock absorbing material. For example, the pair of spacer 1918 may be made of polyether ether ketone (PEEK) material in one embodiment of the present invention.

FIGS. 20A-20D show various views of an alternative dynamic adaptor 2040 according to an alternative embodiment of the present invention. Generally, the alternative dynamic adaptor 2040 may include a stopper 2010 and a cylindrical sleeve 2020. More specifically, the stopper 2010 may be a pivot joint and the cylindrical sleeve 2020 may have a first port 2021, a second port 2022, and a sidewall extension 2024 formed between the first and second ports 2021 and 2022.

The stopper 2010 may be coupled to a first stabilizing rod 2001, and the cylindrical sleeve 2020 may be coupled to the second stabilizing rod 2002. Depending on the design goal, the stopper 2010 and the cylindrical sleeve 2020 may or may not be permanently attached to the first and second stabilizing rods 2001 and 2002. In one embodiment, the stopper 2010 may be connectable to the first elongated member 2001 via a stopper port 2011, and the cylindrical sleeve 2020 may be connectable to the second elongated member 2002 via a sidewall extension port 2023. In another embodiment, the stopper 2010 may be attached to the first elongated member 2001, and the sidewall extension 2023 may be attached to the second elongated member 2002.

The first stabilizing rod 2001 may have a first end segment 2003 and a second segment 2005 as shown in FIG. 20C. The first end segment 2003 may penetrate the cylindrical sleeve 2020 by passing through the second port 2022 and then the first port 2021 of the cylindrical sleeve 2020. When a substantial portion of the second stabilizing rod 2001 passes through the cylindrical sleeve 2020, the second end segment 2005 of stabilizing rod 2001 may still be surrounded by the cylindrical sleeve 2020. The stopper 2010 may have a stopper diameter D202 and the cylindrical sleeve 2010 may have a cylindrical sleeve diameter $D_{201}$. Because the stopper diameter $D_{202}$ may generally be greater than the cylindrical sleeve diameter $D_{201}$, the stopper 2010 may engage the second port 2022 of the cylindrical sleeve 2020 and prevent the second end segment 2005 of the first stabilizing rod 2001 from passing through the first port 2021 of the cylindrical sleeve 2020.

When the second end segment 2005 of the first stabilizing rod 2001 is positioned within the cylindrical sleeve 2020, it may have a range of radial movement 2040. This range of radial movement may be defined by a space between the second end segment 2005 and an inner surface of the cylindrical sleeve 2020. Generally, the first stabilizing rod 2001 may have a core diameter $D_{203}$, which may be smaller than the cylindrical sleeve diameter $D_{201}$. Advantageously, the first stabilizing rod 2001 and the second stabilizing rod 2002 may have a relative movement, which may be a function of the difference between the cylindrical sleeve diameter $D_{201}$ and the core diameter $D_{203}$.

The alternative dynamic adaptor 2040 may include a compressible spacer 2030 inserted between the cylindrical sleeve 2020 and the second end segment 2005 of the first stabilizing rod 2001. The compressible spacer 2030 may be used to stabilize the second end segment 2005 within the cylindrical sleeve 2020 by substantially filling up the space therebetween. More specifically, the compressible spacer 2030 may have a cylindrical body 2031, a pair of guiding members 2035 formed on an outer surface of the cylindrical body 2031, and several compressible flanges 2033 formed on an inner surface of the cylindrical body 2031. The several compressible flanges 2033 may each have a sloped surface 2034. The pair of guiding members 2035 may guide the insertion of the cylindrical body 2031 by engaging a pair of trenches 2025 of the cylindrical sleeve 2020.

After the compressible spacer 2030 is inserted into the cylindrical sleeve 2020, the several compressible flanges 2033 may engage the second end segment 2005 of the stabilizing rod 2001. Because the cylindrical body 2031 and the compressible flanges 2033 of the compressible spacer 2030 substantially reduce the space between the second end segment 2005 and the inner surface of the cylindrical sleeve 2020, the range of radial movement may be substantially reduced. As a result, the first stabilizing rod 2001 may be in a relatively stable position within the cylindrical sleeve 2020. Nevertheless, the compressible spacer 2030 may still reserve a compressible space 2034 and an inter-flange space 2036. Specifically, the compressible space 2034 may be defined between the compressible flange 2033 and the cylindrical body 2031 and the inter-flange space 2036 may be defined between two adjacent compressible flanges 2033. Advantageously, the second end segment 2005 may still have a limited range of radial movement 2041 within the compressible spacer 2030.

FIGS. 20E-20G show a perspective view, a side view and a top view of the alternative dynamic adaptor 2040 connecting the first and second stabilizing rods 2001 and 2002, which may be separately anchored to the two spinal bone segments by the MAPS 2052 and the MAPS 2053. In one embodiment of the present invention, the first stabilizing rod 2001 may have a relative horizontal movement 2043 with respect to the second stabilizing rod 2002. In another embodiment of the present invention, the first stabilizing rod 2001 may have a relative vertical movement 2044 with the second stabilizing rod 2002. In yet another embodiment of the present invention, the first stabilizing rod 2001 may have a relative diagonal movement 2045 with the second stabilizing rod 2002.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An anchoring device, used in conjunction with a stabilizing rod, for stabilizing one or more spinal bone segments, the anchoring device engaging a segment of the stabilizing rod and configured to anchor the stabilizing rod to the one or more spinal bone segments, the anchoring device comprising:
  a screw having a spherical joint and a threaded shaft coupled to the spherical joint; an adaptive member having a first opening, an inner rim defining a second opening and a compression lock disposed adjacent to the first opening, the adaptive member configured to house a substantial portion of the spherical joint between the first and second openings, the compression lock, when deployed, configured to contact the spherical joint and to prevent the spherical joint from passing through the first opening;
  a cradle configured to hold the adaptive member and reinforce the inner rim of the adaptive member;
  a cap configured to engage the cradle, thereby directing a compression force to the deployed compression lock;
  wherein the inner rim has a convex ring configured to pivot the spherical joint along a circular path thereon, thereby allowing limited movement between the threaded shaft and the adaptive member while preventing the spherical joint from passing through the second opening;
  wherein the compression lock has first and second surfaces, and wherein the first surface is configured to receive the compression force and the second surface is configured to engage the spherical joint when the compression lock is deployed; and
  wherein the spherical joint, upon receiving the compression force, is configured to partially depress the convex ring of the inner rim, and wherein the inner rim is configured to assert a reaction force to the spherical joint such that the compression force cooperates with the reaction force to substantially reduce the limited movement between the threaded shaft and the adaptive member.

2. The anchoring device of claim 1, wherein the second surface of the compression lock defines an opening for accessing a bearing surface of the spherical joint.

3. The anchoring device of claim 1, wherein the adaptive member has a substantially cylindrical surface defining the first and second openings such that the substantial portion of the spherical joint are surrounded by the substantially cylindrical surface, and wherein the spherical joint is free of contact of the substantially cylindrical surface.

4. The anchoring device of claim 1, wherein the cradle has a side wall and a base coupled to the side wall, the base having a reinforcement member configured to reinforce the inner rim of the adaptive member.

5. The anchoring device of claim 4, wherein the side wall of the cradle defines a pair of U-shape openings opposing each other, and wherein the U-shape openings are configured to receive the segment of the stabilizing rod engaging the cap and a first surface of the compression lock, thereby transferring the compression force from the cap to the compression member.

6. The anchoring device of claim 4, wherein the cradle has a fastener for affixing the adaptive member within the base of the cradle.

7. An anchoring device, used in conjunction with a stabilizing rod, for stabilizing one or more spinal bone segments, the anchoring device engaging a segment of the stabilizing rod and configured to anchor the stabilizing rod to the one or more spinal bone segments, the anchoring device comprising:
- a screw having a spherical joint and a threaded shaft below the spherical joint;
- a compression member having first and second surfaces, the first surface including a shallow trench for receiving the stabilizing rod, the second surface configured to contact the spherical joint;
- a cylindrical adaptive member configured to house the compression member and a substantial portion of the spherical joint, the cylindrical adaptive member having:
  - a first end defining a first opening,
  - a second end defining a second opening, and having an inner rim including an inner conical surface and a convex pivot ring formed on the inner conical surface, the convex ring configured to contact the spherical joint along a circular path thereon, thereby allowing a limited movement between the threaded shaft and the cylindrical adaptive member while preventing the spherical joint from passing through the second opening, and
  - a plurality of locking members disposed adjacent to the first end, each locking member movable between a deployed position and an undeployed position, the plurality of locking members configured to prevent the compression member from passing through the first opening when in the deployed position, thereby locking a substantial portion of the spherical joint within the cylindrical adaptive member;
- a cradle having:
  - a base configured to hold the cylindrical adaptive member, the base including a reinforcement member configured to reinforce the inner rim of the cylindrical adaptive member;
  - a side coupled to the base, and including a fastener for affixing and retaining the cylindrical adaptive member within the base of the cradle; and
- a cap configured to engage the cradle and direct a compression force to the first surface of the compression member via the received stabilizing rod.

* * * * *